US012570693B2

(12) United States Patent
Stoynova et al.

(10) Patent No.: US 12,570,693 B2
(45) Date of Patent: Mar. 10, 2026

(54) METHOD OF PRODUCING A TRIPEPTIDE GAMMA-GLU-VAL-GLY USING ENTEROBACTERIACEAE

(71) Applicant: AJINOMOTO CO., INC., Tokyo (JP)

(72) Inventors: Natalia V. Stoynova, Moscow (RU); Elena V. Sycheva, Moscow (RU); Natalia V. Geraskina, Moscow (RU); Elena V. Matrosova, Moscow (RU); Sergey V. Smirnov, Moscow (RU); Ayako Sato, Kawasaki (JP); Eri Higashiura, Kawasaki (JP); Misato Okamoto, Kawasaki (JP); Takayuki Ito, Kawasaki (JP); Erika Watanabe, Kawasaki (JP); Yuki Oda, Kawasaki (JP); Uno Tagami, Kawasaki (JP); Tatsuki Kashiwagi, Kawasaki (JP); Masayuki Sugiki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 899 days.

(21) Appl. No.: 17/100,239

(22) Filed: Nov. 20, 2020

(65) Prior Publication Data

US 2021/0070800 A1     Mar. 11, 2021

Related U.S. Application Data

(63) Continuation of application No. PCT/JP2019/020305, filed on May 22, 2019.

(30) Foreign Application Priority Data

May 23, 2018     (RU) ................................ 2018118992

(51) Int. Cl.
| | |
|---|---|
| *C12P 21/02* | (2006.01) |
| *C07K 5/093* | (2006.01) |
| *C07K 14/245* | (2006.01) |
| *C12N 9/00* | (2006.01) |
| *C12N 9/04* | (2006.01) |
| *C12N 15/31* | (2006.01) |

(52) U.S. Cl.
CPC ................................. *C07K 5/0819* (2013.01)

(58) Field of Classification Search
None
See application file for complete search history.

(56) References Cited

U.S. PATENT DOCUMENTS

| | | | | |
|---|---|---|---|---|
| 9,580,696 | B2 * | 2/2017 | Nozaki | C07K 5/0819 |
| 9,677,106 | B2 * | 6/2017 | Nozaki | C12P 21/02 |
| 10,113,161 | B2 * | 10/2018 | Sasahara | C07K 5/0215 |
| 10,508,295 | B2 * | 12/2019 | Tsuji | C12P 21/02 |
| 11,142,755 | B2 * | 10/2021 | Sato | C12N 9/93 |
| 11,788,109 | B2 * | 10/2023 | Sasahara | C12N 1/205 |
| | | | | 435/68.1 |
| 2015/0361133 | A1 | 12/2015 | Iwasaki | |
| 2016/0340707 | A1 | 11/2016 | Tsuji et al. | |

FOREIGN PATENT DOCUMENTS

| | | | |
|---|---|---|---|
| EP | | 3101130 A1 | 12/2016 |
| EP | | 3345996 A1 | 7/2018 |
| WO | WO 2014/025023 A1 | | 2/2014 |
| WO | WO 2014/123175 A1 | | 8/2014 |
| WO | WO 2015/133547 A1 | | 9/2015 |
| WO | WO 2015/136841 A1 | | 9/2015 |

OTHER PUBLICATIONS

UniProt Database Accession No. P07913, Apr. 2017, 4 pages (Year: 2017).*
UniProt Database Accession No. P0AB78, Apr. 2017, 2 pages (Year: 2017).*
Zhang et al., Biotechnol. Bioprocess Eng. 22:390-396, 2017 (Year: 2017).*
Deininger et al., PLoS ONE 6:e18960, 2011, 7 pages (Year: 2011).*
Wang et al., Appl. Microbiol. Biotechnol. 97:8057-8067, 2013 (Year: 2013).*
Koronakis et al., "Structure and Function of TolC: The Bacterial Exit Duct for Proteins and Drugs," Annu. Rev. Biochem. 73:467-489 , 2004 (Year: 2004).*
Sharff et al., "The role of the TolC family in protein transport and multidrug efflux From stereochemical certainty to mechanistic hypothesis," Eur. J. Biochem. 268:5011-5026, 2001 (Year: 2001).*
Du et al., "Structure of the AcrAB-ToIC multidrug efflux pump," Nature 509:512-515, 2014 (Year: 2014).*
Lin. Z., et al., "Metabolic engineering of *Escherichia coli* for poly(3-hydroxybutyrate) production via threonine bypass", Microbial Cell Factories, 2015, 14:185, pp. 1-12.
Edgar, Alasdair J, "Mice have a transcribed L-threonine aldolase/GL YI gene, but the human GLYI gene is a non-processed pseudogene", BMC Genomics, 2005, 6:32, pp. 1-12.
Sofyanovich, Olga A., et al., "Multiple pathways for the formation of the y-glutamyl peptides y-glutamyl-valine and y-glutamyl-valyl glycine in *Saccharomyces cerevisiae*", PLOS ONE, May 9, 2019, pp. 1-18.

(Continued)

*Primary Examiner* — David Steadman
(74) *Attorney, Agent, or Firm* — Oblon, McClelland, Maier & Neustadt, L.L.P.

(57)     ABSTRACT

A method for producing γ-Glu-Val-Gly is described, wherein the method includes the steps of cultivating a γ-Glu-Val-Gly-producing bacterium belonging to the family Enterobacteriaceae in a culture medium so that the γ-Glu-Val-Gly accumulates in the culture medium or the cells of the bacterium, or both, and collecting the γ-Glu-Val-Gly from the culture medium or the cells of the bacterium, or both. The bacterium has been modified to overexpress a gene encoding a protein having L-threonine 3-dehydrogenase activity and a gene encoding a protein having 2-amino-3-oxobutanoate coenzyme A ligase activity.

10 Claims, No Drawings

Specification includes a Sequence Listing.

(56)  References Cited

OTHER PUBLICATIONS

Miyamura, N., et al., "Determination and quantification of kokumi peptide, g-glutamyl-valyl-glycine, in brewed alcoholic beverages", J. Biosci. and Bioeng., 2015, vol. 120, No. 3, pp. 311-314.

Miyamura, N., et al., "Determination and Quantification of a Kokumi Peptide, y-Glutamyl-Valy-Glycine, in Fermented Shrimp Paste Condiments", Food Sci. and Technol. Res., 2014, 20(3) pp. 699-703.

International Search Report issued Jul. 4, 2019 in PCT/JP2019/020305 filed May 22, 2019.

Written Opinion of the International Search Authority issued Jul. 4, 2019 in PCT/JP2019/020305 filed May 22, 2019.

* cited by examiner

METHOD OF PRODUCING A TRIPEPTIDE GAMMA-GLU-VAL-GLY USING ENTEROBACTERIACEAE

FIELD OF THE INVENTION

The present invention relates to the microbiological industry, and specifically to a method for producing a tripeptide, and more specifically, the tripeptide γ-Glu-Val-Gly. The method of the present invention uses a bacterium of the genus Enterobacteriaceae that has been modified, at least, to overexpress the tdh and kbl genes.

DESCRIPTION OF THE RELATED ART

Methods for fermentative production of amino acids and peptides utilizing mutant microorganism, or microorganisms resistant to various drugs, have been previously reported. Conventional methods for producing such mutant strains include subjecting microorganisms to a mutagenesis treatment such as UV-irradiation or treatment with nitrosoguanidine (N-methyl-N'-nitro-N-nitrosoguanidine), followed by selecting the desired strain by using a suitable selection medium. Alternatively, mutant strains can be bred by the use of genetic engineering techniques, including overexpressing, genes involved in the biosynthesis pathway of the desired amino acid and peptides.

Production of a tripeptide such as γ-Glu-Val-Gly has been achieved previously via chemical and enzymatic methods, but not using fermentation of microorganisms. For example, WO 2015133547 A1 describes a multi-step method that uses various synthase enzymes to produce γ-Glu-Val and then γ-Glu-Val-Gly. WO 2014025023 A1 describes methods of producing γ-Glu-Val-Gly crystals via basic enzymatic and chemical methods. However, the use of fermentation of microorganisms engineered to produce γ-Glu-Val-Gly has not been previously described.

γ-Glu-Val-Gly is known to be useful in both the food and fragrance industries. For example, the tripeptide has been reported to have superior kokumi qualities, and hence has been used to flavor tea (WO 2015136841 A1), alcoholic beverages (Miyamura et al., J. Biosci. and Bioeng. (2015) 120(3):311-314), condiments (Miyamura et al., Food Sci. and Technol. Res. (2014) 20(3):699-703), and spices (WO 2014123175 A1). Hence, efficient and successful overproduction of the tripeptide γ-Glu-Val-Gly by fermentation of microorganisms is highly desirable.

The effect of overexpression of the gene(s) encoding L-threonine 3-dehydrogenase and/or 2-amino-3-oxobutanoate coenzyme A ligase on production of tripeptide γ-Glu-Val-Gly by fermentation of a bacterium belonging to the genus Enterobacteriaceae has not been previously reported.

SUMMARY OF THE INVENTION

It is an aspect of the present invention to provide a method for producing γ-Glu-Val-Gly comprising cultivating a γ-Glu-Val-Gly-producing bacterium belonging to the family Enterobacteriaceae in a culture medium so that the γ-Glu-Val-Gly is produced and accumulates in the culture medium or the cells of the bacterium, or both, and collecting the γ-Glu-Val-Gly from the culture medium or the cells of the bacterium, or both, wherein the bacterium has been modified to overexpress a gene encoding a protein having L-threonine 3-dehydrogenase activity and a gene encoding a protein having 2-amino-3-oxobutanoate coenzyme A ligase activity.

It is a further aspect of the present invention to provide the method as described above, wherein said protein having L-threonine 3-dehydrogenase activity is encoded by a tdh gene, and said protein having 2-amino-3-oxobutanoate coenzyme A ligase activity is encoded by a kbl gene. It is a further aspect of the present invention to provide the method as described above, wherein said protein having L-threonine 3-dehydrogenase activity is selected from the group consisting of a protein comprising the amino acid sequence shown in SEQ ID NO: 2, a protein comprising the amino acid sequence shown in SEQ ID NO: 2, but which includes substitution, deletion, insertion and/or addition of 1 to 50 amino acid residues, and wherein said protein has L-threonine 3-dehydrogenase activity, and a protein comprising an amino acid sequence having an identity of not less than 50% with respect to the entire amino acid sequence shown in SEQ ID NO: 2, and wherein said protein has L-threonine 3-dehydrogenase activity; and wherein said protein having 2-amino-3-oxobutanoate coenzyme A ligase activity is selected from the group consisting of a protein comprising the amino acid sequence shown in SEQ ID NO: 4, a protein comprising the amino acid sequence shown in SEQ ID NO: 4, but which includes substitution, deletion, insertion and/or addition of 1 to 50 amino acid residues, and wherein said protein has 2-amino-3-oxobutanoate coenzyme A ligase activity, and a protein comprising an amino acid sequence having an identity of amino acid residues of not less than 60% with respect to the entire amino acid sequence shown in SEQ ID NO: 4, and wherein said protein has 2-amino-3-oxobutanoate coenzyme A ligase activity.

It is a further aspect of the present invention to provide the method as described above, wherein said protein having L-threonine 3-dehydrogenase activity is encoded by a DNA selected from the worm consisting of a DNA comprising the nucleotide sequence shown in SEQ ID NO: 1, a DNA comprising a nucleotide sequence that is able to hybridize under stringent conditions with a nucleotide sequence complementary to the sequence shown in SEQ ID NO: 1, a DNA encoding a protein comprising the amino acid sequence shown in SEQ ID NO: 2, but which includes substitution, deletion, insertion and/or addition of 1 to 50 amino acid residues, and wherein said protein has L-threonine 3-dehydrogenase activity, and a DNA which is a variant nucleotide sequence of SEQ ID NO: 1 due to the degeneracy of the genetic code; and wherein said protein having 2-amino-3-oxobutanoate coenzyme A ligase is encoded by a DNA selected from the group consisting of a DNA comprising the nucleotide sequence shown in SEQ ID NO: 3, a DNA comprising a nucleotide sequence that is able to hybridize under stringent conditions with a nucleotide sequence complementary to the sequence shown in SEQ ID NO: 3, a DNA encoding a protein comprising the amino acid sequence shown in SEQ ID NO: 4, but which includes substitution, deletion, insertion and/or addition of 1 to 50 amino acid residues, and wherein said protein has 2-amino-3-oxobutanoate coenzyme A ligase activity, and a DNA which is a variant nucleotide sequence of SEQ ID NO: 3 due to the degeneracy of the genetic code.

If is a further aspect of the present invention to provide the method as described above, wherein the gene encoding the protein having L-threonine 3-dehydrogenase activity and the gene encoding the protein having 2-amino-3-oxobutanoate coenzyme A ligase activity are each overexpressed by a method selected from the group consisting of increasing the copy number of the gene or genes in the bacterium, modifying an expression regulatory region of the gene or genes in the bacterium, and combinations thereof, wherein the expression of said genes is increased as compared with a non-modified bacterium.

It is a further aspect of the present invention to provide the method as described above, wherein said bacterium has been modified further by a method selected from the group consisting of attenuating expression of a gcvP gene, attenuating expression of sucAB operon genes, overexpressing a tolC gene, overexpressing ilvGMEDA operon genes, and combinations thereof.

It is a further aspect of the present invention to provide the method as described above, wherein said ilvGMEDA operon genes contains an ilvG gene that encodes an acetolactate synthase II, wherein the activity of said acetolactate synthase II has been restored.

It is a further aspect of the present invention to provide the method as described above, wherein said bacterium belongs to the genus *Escherichia* or *Pantoea*.

It is a further aspect of the present invention to provide the method as described above, wherein said bacterium is *Escherichia coli* or *Pantoea ananatis*.

Still other objects, features, and attendant advantages of the present invention will become apparent to those skilled in the art from a reading of the following detailed description of embodiments.

DETAILED DESCRIPTION OF EXEMPLARY EMBODIMENTS

1. Bacterium

In the method as described herein, any γ-Glu-Val-Gly-producing bacterium that has been modified to overexpress both a gene encoding a protein having L-threonine 3-dehydrogenase activity and a gene encoding a protein having 2-amino-3-oxobutanoate coenzyme A ligase activity can be used.

The bacterium to be modified (i.e. the bacterium before introducing the modification of overexpressing both the genes) is not particularly limited, so long as the bacterium can be modified to overexpress both a gene encoding a protein having L-threonine 3-dehydrogenase activity and a gene encoding a protein having 2-amino-3-oxobutanoate coenzyme A ligase activity, and the bacterium thus modified (i.e. the bacterium after introducing the modification of overexpressing both the genes) is able to produce a tripeptide γ-Glu-Val-Gly. Examples of the bacterium are described hereinafter.

The phrase "a bacterium is able to produce a tripeptide γ-Glu-Val-Gly" used for a bacterium after introducing a modification can mean that the bacterium did not have an ability to produce a tripeptide γ-Glu-Val-Gly before introducing the modification, but has obtained the ability to produce a tripeptide γ-Glu-Val-Gly by introducing the modification. Also, the phrase "a bacterium is able to produce a tripeptide γ-Glu-Val-Gly" used for a bacterium after introducing a modification can mean that the bacterium is rendered able to produce a tripeptide γ-Glu-Val-Gly by introducing the modification.

The phrase "a γ-Glu-Val-Gly-producing bacterium" can be equivalent to the phrase "a bacterium that is able to produce a tripeptide γ-Glu-Val-Gly" or the phrase "a bacterium having an ability to produce a tripeptide γ-Glu-Val-Gly". The phrase "a γ-Glu-Val-Gly-producing bacterium" can mean a bacterium that is able to produce a tripeptide by fermentation of the bacterium in a culture medium. The phrase "a γ-Glu-Val-Gly-producing bacterium" can also mean a bacterium that is able to produce, excrete or secrete, and/or cause accumulation of the tripeptide γ-Glu-Val-Gly in a culture medium and/or the bacterial cells when the bacterium is cultivated in the medium. The phrase "a γ-Glu-Val-Gly-producing bacterium" can specifically mean a bacterium that is able to produce, excrete or secrete, and/or cause accumulation of the tripeptide γ-Glu-Val-Gly in a culture medium and/or the bacterial cells to such a level that the tripeptide γ-Glu-Val-Gly can be collected from the culture medium and/or the bacterial cells when the bacterium is cultivated in the medium. The phrase "a bacterium is cultivated in a medium" can be equivalent to the phrase "a bacterium is cultured in a medium", and these phrases are known to persons of ordinary skill in the art. The phrase "a γ-Glu-Val-Gly-producing bacterium" can also specifically mean a bacterium that is able to produce, excrete or secrete, and/or cause accumulation of the tripeptide γ-Glu-Val-Gly in a culture medium in an amount larger than a non-modified strain, for example, a wild-type or parental strain such as *Escherichia coli* (*E. coli*) K-12 including *E. coli* K-12 MG1655. The phrase "a γ-Glu-Val-Gly-producing bacterium" can also specifically mean a bacterium that is able to produce and cause accumulation in the medium and/or the bacterial cells of an amount not less than 0.01 g/L of the tripeptide γ-Glu-Val-Gly, for example, not less than 0.1 g/L, or not less than 0.5 g/L, or not less than 1.0 g/L of the tripeptide γ-Glu-Val-Gly. The phrase "a γ-Glu-Val-Gly-producing bacterium" can particularly mean a bacterium that is able to produce and cause accumulation in the medium of an amount not less than 0.01 g/L of the tripeptide γ-Glu-Val-Gly, for example, not less than 0.1 g/L, or not less than 0.5 g/L, or not less than 1.0 g/L of the tripeptide γ-Glu-Val-Gly.

The phrase "a tripeptide γ-Glu-Val-Gly", which can be used interchangeably or equivalently to the phrase "γ-Glu-Val-Gly" (also abbreviated as "γ-EVG"), can mean a tripeptide, which is a peptide containing three amino acid residues covalently bonded to one another in a chain configuration, wherein the tripeptide as described herein contains the glycine (Gly) residue, the amino group of which is bonded to the carboxylic group of the valine (Val) residue, the amino group of which is bound to the carboxylic group at the γ-carbon atom of the glutamic acid (Glu) residue (PubChem CID: 25099093).

The bacterium can produce a tripeptide γ-Glu-Val-Gly in a free form, or a salt or hydrate thereof, or an adduct thereof (e.g. an adduct formed by the γ-Glu-Val-Gly and another organic or inorganic compound), or a mixture of these. Therefore, the phrase "γ-Glu-Val-Gly" can include not only a tripeptide γ-Glu-Val-Gly in a free form, but may also include a salt or hydrate of the γ-Glu-Val-Gly, or an adduct thereof (e.g. an adduct formed by the γ-Glu-Val-Gly and another organic or inorganic compound). That is, the phrase "γ-Glu-Val-Gly" can mean a tripeptide γ-Glu-Val-Gly in a free form, a salt or hydrate thereof, an adduct thereof, or a mixture thereof. The phrase "γ-Glu-Val-Gly" can particularly mean a tripeptide γ-Glu-Val-Gly in a free form, a salt thereof, or a mixture thereof. It is also acceptable that the bacterium can produce a tripeptide γ-Glu-Val-Gly either alone or as a mixture of the γ-Glu-Val-Gly and one or more kinds of other amino acids or peptides. The phrase "L-amino acid" can mean an amino acid in L-form (so-called L-enantiomer of an amino acid) such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine. The phrase "peptide" can include, for example, a dipeptide such as, for example, γ-Glu-Val and Val-Gly.

The bacterium may inherently be able to produce a tripeptide γ-Glu-Val-Gly or may be modified to become able to produce a tripeptide γ-Glu-Val-Gly. Such modification can be attained by, for example, mutation or DNA recombination techniques. That is, the bacterium can be obtained by overexpressing a gene encoding a protein having L-threonine 3-dehydrogenase activity and a gene encoding a protein having 2-amino-3-oxobutanoate coenzyme A ligase activity in a bacterium that inherently is able to produce a tripeptide γ-Glu-Val-Gly, or in a bacterium that has been modified to become able to produce a tripeptide γ-Glu-Val-Gly. Alternatively, the bacterium can be obtained by overexpressing a gene encoding a protein having L-threonine 3-dehydrogenase activity and a gene encoding a protein having 2-amino-3-oxobutanoate coenzyme A ligase activity to render the bacterium able to produce a tripeptide γ-Glu-Val-Gly. That is, the bacterium can be modified to overexpress the gene encoding a protein having L-threonine 3-dehydrogenase activity and the gene encoding a protein having 2-amino-3-oxobutanoate coenzyme A ligase activity so that the bacterium thus modified is able to produce a tripeptide γ-Glu-Val-Gly.

The bacterium as described herein can be, for example, a gram-negative bacterium, specific examples of which include a bacterium belonging to the family Enterobacteriaceae. The explanations given hereinafter to the bacterium can be applied mutatis mutandis to any bacterium that can be used equivalently in the method as described herein.

In the method as described herein, the bacteria belonging to the family Enterobacteriaceae can be from the genera *Enterobacter, Erwinia, Escherichia, Klebsiella, Morganella, Pantoea, Photorhabdus, Providencia, Salmonella, Yersinia*, and so forth, and can be able to produce a tripeptide γ-Glu-Val-Gly. Specifically, those classified into the family Enterobacteriaceae according to the taxonomy used in the NCBI (National Center for Biotechnology Information) database can be used. Examples of bacterial strains from the family Enterobacteriaceae which can be modified include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, can include those described in the work of Neidhardt et al. (Bachmann, B. J., Derivations and genotypes of some mutant derivatives of *Escherichia coli* K-12, p. 2460-2488. In F. C. Neidhardt et al. (ed.), *Escherichia coli* and *Salmonella*: cellular and molecular biology, 2$^{nd}$ ed. ASM Press, Washington, D.C., 1996). The species *Escherichia coli* (*E. coli*) is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain. These strains are available from, for example, the American Type Culture Collection (ATCC) as explained above. Examples of the *Enterobacter* bacteria include *Enterobacter agglomerans, Enterobacter aerogenes*, and so forth. Examples of the *Pantoea* bacteria include *Pantoea ananatis* (*P. ananatis*), and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. When a *P. ananatis* strain is bred by genetic engineering techniques. *P. ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently reclassified as *P. ananatis* on the basis of nucleotide sequencing of 16S rRNA and so forth as described above.

These strains are available from, for example, the American Type Culture Collection (ATCC: Address: P.O. Box 1549, Manassas, VA 20108, United States of America). That is, registration numbers are assigned to the respective strains, and the strains can be ordered by using these registration numbers (refer to atcc.org). The registration numbers of the strains are listed in the catalogue of the American Type Culture Collection.

The bacterium as described herein has been modified to overexpress a gene encoding a protein having L-threonine 3-dehydrogenase activity and a gene encoding a protein having 2-amino-3-oxobutanoate coenzyme A ligase activity.

The phrase "a protein having L-threonine 3-dehydrogenase activity" can mean a protein that causes catalysis of the following reaction: L-threonine+NAD$^+$⇋L-2-amino-3-oxobutanoate+NADH+2 H$^+$ (Enzyme Commission (EC) number 1.1.1.103; Boylan S. A. and Dekker E. E., L-Threonine dehydrogenase. Purification and properties of the homogeneous enzyme from *E. coli* K-12, *J. Biol. Chem.*, 1981, 256(4):1809-1815). For example, a protein having L-threonine 3-dehydrogenase activity can mean the protein having the amino acid sequence shown in SEQ ID NO: 2 and homologues thereof that can cause catalysis of the reaction of the NAD+-dependent oxidation of L-threonine to L-2-amino-3-oxobutanoate. The activity of a protein having L-threonine 3-dehydrogenase activity can be determined by evaluating colorimetrically the formation of aminoacetone from L-threonine or monitoring the formation of NADH using a spectrophotometer (see Boylan S. A. and Dekker E. E., 1981, and references therein). The phrase "a protein having 2-amino-3-oxobutanoate coenzyme A ligase activity" can mean a protein that causes catalysis of the following reaction: glycine+acetyl-coenzyme A⇋L-2-amino-3-oxobutanoate+coenzyme A+H$^+$ (EC 2.3.1.29; acetyl-coenzyme A is also referred to as Ac-CoA; Mukherjee J. J. and Dekker E. E. Purification, properties, and N-terminal amino acid sequence of homogeneous *E. coli* 2-amino-3-ketobutyrate CoA ligase, a pyridoxal phosphate-dependent enzyme, *J. Biol. Chem.*, 1987, 262:14441-14447). For example, a protein having 2-amino-3-oxobutanoate coenzyme A ligase activity can mean the protein having the amino acid sequence shown in SEQ ID NO: 4 and homologues thereof that can cause catalysis of the reaction of the cleavage of 2-amino-3-oxobutanoate to glycine and acetyl-coenzyme A. The activity of a protein having 2-amino-3-oxobutanoate coenzyme A ligase activity can be determined by evaluating colorimetrically the formation of aminoacetone from glycine and Ac-CoA or observing the condensation reaction at 412 nm between coenzyme A (also referred to as CoA) and 5,5'-dithiobis-(2-nitrobenzoic acid) (see, for example, Mukherjee J. J. and Dekker E. E., 1987, and references therein).

The protein concentration can be determined by the Bradford protein assay or the method of Lowry using bovine serum albumin (BSA) as a standard and a Coomassie dye (Bradford M. M., *Anal. Biochem.*, 1976, 72:248-254; Lowry O. H. et al., *J. Biol. Chem.* 1951, 193:265-275).

An example of the protein having L-threonine 3-dehydrogenase activity can include the protein having the amino acid sequence shown in SEQ ID NO: 2. The amino acid sequence shown in SEQ ID NO: 2 can be encoded by the nucleotide sequence shown in SEQ ID NO: 1, which corresponds to the tdh gene. That is, an example of the protein having L-threonine 3-dehydrogenase activity can include a tdh gene. The tdh gene of $E. coli$ encodes the L-threonine 3-dehydrogenase TDH, NAD (P)-binding (KEGG, Kyoto Encyclopedia of Genes and Genomes, entry No. b3616; Protein Knowledgebase, UniProtKB/Swiss-Prot, accession No. P07913). The tdh gene (GenBank, accession No. NC_000913.3; nucleotide positions: 3790320 to 3791345, complement; Gene ID: 948139) is located between the kb/gene and the waaH gene on the same strand of the chromosome of $E. coli$ strain K-12. The nucleotide sequence of the tdh gene (SEQ ID NO: 1) and the amino acid sequence of the TDH protein (SEQ ID NO: 2) encoded by the tdh gene of $E. coli$ are known. Moreover, homologues of TDH from different bacterial species are also known such as, for example, the homologues native to the bacteria belonging to the family Enterobacteriaceae, including the species $E. coli$ having the TDH of SEQ ID NO: 2 (identity: 100%), Shigella flexneri (identity: 99%), Salmonella enteric (identity: 98%), Klebsiella pneumonia (identity: 97%), Enterobacter cloacae (identity: 96%), P. ananatis (identity: 86%); the family Burkholderiaceae, including the species Burkholderia mallei (identity: 77%), Paraburkholderia xenovorans (identity: 76%); the family Rhizobiaceae, including the species Rhizobium etli (identity: 71%); the family Xanthomonadaceae, including the species Xanthomonas axonopodis (identity: 64%); and so forth (see, for example, the NCBI database, National Center for Biotechnology Information). Therefore, examples of the proteins having L-threonine 3-dehydrogenase activity can also include the proteins that are homologues of the protein having the amino acid sequence shown in SEQ ID NO: 2.

An example of the protein having 2-amino-3-oxobutanoate coenzyme A ligase activity can be the protein having the amino acid sequence shown in SEQ ID NO: 4. The amino acid sequence shown in SEQ ID NO: 4 can be encoded by the nucleotide sequence shown in SEQ ID NO: 3 which corresponds to the kbl gene. That is, an example of the protein having 2-amino-3-oxobutanoate coenzyme A ligase activity can include a kbl gene. The kbl gene of $E. coli$ encodes the 2-amino-3-oxobutanoate coenzyme A ligase KBL (synonyms: 2-amino-3-ketobutyrate coenzyme A ligase, 2-amino-3-oxobutanoate glycine-lyase (CoA-acetylating), glycine C-acetyltransferase, aminoacetone synthetase, aminoacetone synthase) (KEGG, entry No. b3617; Protein Knowledgebase, UniProtKB/Swiss-Prot, accession No. P0AB77). The kbl gene (GenBank, accession No. NC_000913.3; nucleotide positions: 3791355 to 3792551, complement; Gene ID: 948138) is located between the yibB gene and the tdh gene on the same strand of the chromosome of $E. coli$ strain K-12. The nucleotide sequence of the kbl gene (SEQ ID NO: 3) and the amino acid sequence of the KBL protein (SEQ ID NO: 4) encoded by the kbl gene of $E. coli$ are known. Moreover, homologues of KBL from different bacterial species are also known such as, for example, the homologues native to the bacteria belonging to family Enterobacteriaceae, including the species $E. coli$ having the KBL of SEQ ID NO: 4 (identity: 100%), Shigella dysenteriae (identity: 99%), Citrobacter farmer (identity: 97%), Salmonella enterica (identity: 97%), P. ananatis (identity: 82%), the family Yersiniaceae, including the species Serratia marcescens (identity: 88%); from the family Morganellaceae, including species Xenorhabdus khoisanae (identity: 83%); from the family Erwiniaceae, including the species Erwinia sp. 9145 (identity: 82%); from the family Xanthomonadaceae, including the species Lysobacter spongiicola (identity: 67%), Stenatrophomonas maltophilia (identity: 66%); and so forth (see, for example, the NCBI database). Therefore, examples of the proteins having 2-amino-3-oxobutanoate coenzyme A ligase activity can also be the proteins that are homologues of the protein having the amino acid sequence shown in SEQ ID NO: 4.

The phrase "a bacterium has been modified to overexpress a gene encoding a protein having L-threonine 3-dehydrogenase activity and a gene encoding a protein having 2-amino-3-oxobutanoate coenzyme A ligase activity" can mean that the bacterium has been modified in such a way that in the modified bacterium the total activity of the corresponding gene product that causes catalysis of the reaction of the NAD+-dependent oxidation of L-threonine to L-2-amino-3-oxobutanoate and the total activity of the corresponding gene product that causes catalysis of the reaction of the cleavage of 2-amino-3-oxobutanoate to glycine and acetyl-coenzyme A are both increased, or the expression level (i.e. expression amount) of the gene encoding a protein having L-threonine 3-dehydrogenase activity and the expression level (i.e. expression amount) of the gene encoding a protein having 2-amino-3-oxobutanoate coenzyme A ligase activity are both increased, as compared with a non-modified strain. The phrase "a non-modified strain" can refer to a bacterial strain that can serve as a reference for the above comparison. The phrase "a non-modified strain" is also referred to as "a non-modified bacterium" or "a non-modified bacterial strain". Examples of the non-modified strain can include a wild-type or parental strain of a bacterium belonging to the family Enterobacteriaceae such as a bacterium belonging to the genus Escherichia or Pantoea including $E. coli$ and P. ananatis. Specific examples of the non-modified strain can include the strains $E. coli$ MG1655 (ATCC 47076) and W3110 (ATCC 27325) and the strain P. ananatis AJ13355 (FERM BP-6614).

The bacterium modified to overexpress a gene encoding a protein having L-threonine 3-dehydrogenase activity and a gene encoding a protein having 2-amino-3-oxobutanoate coenzyme A ligase activity can be a bacterium in which the total activity of the corresponding gene product that causes catalysis of the reaction of the NAD+-dependent oxidation of L-threonine to L-2-amino-3-oxobutanoate and the total activity of the corresponding gene product that causes catalysis of the reaction of the cleavage of 2-amino-3-oxobutanoate to glycine and acetyl-coenzyme A can be both increased by, for example, increasing (i.e. enhancing) the expression level of the gene encoding the protein having L-threonine 3-dehydrogenase activity and the gene encoding the protein having 2-amino-3-oxobutanoate coenzyme A ligase activity, or increasing the activity per molecule (may be referred to as a specific activity) of the proteins encoded by said genes, as compared with a non-modified strain, for example, a wild-type or parental strain. An increase in total activity of a protein can be measured as, for example, an increase in the activity of the protein per cell, which may be an average activity of the protein per cell. The bacterium may be modified so that the activity of the protein having L-threonine 3-dehydrogenase activity per cell and/or the activity of the protein having 7-amino-3-oxobutanoate coenzyme A ligase activity per cell are/is increased to, for example, 150% or more, 200% or more, 300% or more, of the activity of that protein(s) in a non-modified strain.

The phrase "a bacterium has been modified to overexpress a gene encoding a protein having L-threonine 3-dehydrogenase activity and a gene encoding a protein having 2-amino-3-oxobutanoate coenzyme A ligase activity" can also mean that the bacterium has been modified in such a way that in the modified bacterium the expression level (i.e. expression amount) of a gene encoding a protein having L-threonine 3-dehydrogenase activity and the expression level (i.e. expression amount) of a gene encoding a protein having 2-amino-3-oxobutanoate coenzyme A ligase activity are both increased as compared with a non-modified strain, for example, a wild-type or parental strain. Therefore, the phrase "a gene is overexpressed" can be equivalent to the phrase "the expression of a gene is enhanced or increased" or the phrase "the expression level of a gene is enhanced or increased". An increase in the expression level of a gene can be measured as, for example, an increase in the expression level of the gene per cell, which may be an average expression level of the gene per cell. The bacterium may be modified so that the expression level of the gene encoding a protein having L-threonine 3-dehydrogenase activity per cell and/or the expression level of the gene encoding a protein having 2-amino-3-oxobutanoate coenzyme A ligase activity per cell are/is increased to, for example, 150% or more, 200% or more, 300% or more, of the expression level of that gene(s) in a non-modified strain.

The aforementioned descriptions concerning overexpression of a gene encoding a protein having L-threonine 3-dehydrogenase activity and a gene encoding a protein having 2-amino-3-oxobutanoate coenzyme A ligase activity can also be independently applied to each of these genes.

Methods for modifying a bacterium to overexpress both a gene encoding a protein having L-threonine 3-dehydrogenase activity and a gene encoding a protein having 2-amino-3-oxobutanoate coenzyme A ligase activity, and methods which can be used to enhance expression of the gene encoding a protein having L-threonine 3-dehydrogenase activity and the gene encoding a protein having 2-amino-3-oxobutanoate coenzyme A ligase activity in the bacterium as described herein may depend on the bacterium that is chosen for the modification. Any method for gene overexpression may be used, so long as the overexpression of the gene can be attained using that method. Therefore, the gene encoding a protein having L-threonine 3-dehydrogenase activity and the gene encoding a protein having 2-amino-3-oxobutanoate coenzyme A ligase activity can be overexpressed using one method for gene overexpression, or the genes can be overexpressed using different methods for gene overexpression.

Methods which can be used to enhance expression of a gene can include, but are not limited to, increasing the copy number of the gene, such as the copy number of the gene in the chromosome of the bacterium and/or in the autonomously replicating plasmid harbored by the bacterium. The copy number of a gene can be increased by, for example, introducing the gene into the chromosome of the bacterium and/or introducing an autonomously replicating vector containing the gene into the bacterium. Such increasing of the copy number of a gene can be carried out according to genetic engineering methods known to the one of ordinary skill in the art.

Examples of the vectors can include, but are not limited to, broad-host-range plasmids such as pMW118/119, pBR322, pUC19, and the like. Multiple copies of a gene encoding a protein having L-threonine 3-dehydrogenase activity and/or a gene encoding a protein having 2-amino-3-oxobutanoate coenzyme A ligase activity can also be introduced into the chromosomal DNA of a bacterium by, for example, homologous recombination, Mu-driven integration, or the like. Only one copy, or two or more copies of each gene may be introduced. For example, homologous recombination can be carried out using a sequence that is present in multiple copies in the chromosomal DNA as a target to introduce multiple copies of a gene into the chromosomal DNA. Sequences with multiple copies in the chromosomal DNA can include, but are not limited to, repetitive DNA or inverted repeats present at the end of a transposable element. In addition, it is possible to incorporate a gene into a transposon and allow it to be transferred to introduce multiple copies of the gene into the chromosomal DNA. By using Mu-driven integration, more than 3 copies of the gene can be introduced into the chromosomal DNA during a single act (Akhverdyan V. Z. et al., *Biotechnol. (Russian)*, 2007, 3:3-20).

The bacterium as described herein can be modified to overexpress a gene encoding a protein having L-threonine 3-dehydrogenase activity and a gene encoding a protein having 2-amino-3-oxobutanoate coenzyme A ligase activity so that the genes are present in the bacterium after introduction of the genes. Also, the bacterium can be modified in such a way that the activity of the protein having L-threonine 3-dehydrogenase activity and the activity of the protein having 2-amino-3-oxobutanoate coenzyme A ligase activity can be determined in the modified bacterium. That is, any bacterium that does not natively or naturally have a gene encoding a protein having L-threonine 3-dehydrogenase activity and a gene encoding a protein having 2-amino-3-oxobutanoate coenzyme A ligase activity can be used, so long as the bacterium can be modified to overexpress the gene encoding a protein having L-threonine 3-dehydrogenase activity and the gene encoding a protein having 2-amino-3-oxobutanoate coenzyme A ligase activity so that the activity of the protein having L-threonine 3-dehydrogenase activity and the activity of the protein having the activity a 2-amino-3-oxobutanoate coenzyme A ligase can be determined in the modified bacterium and the modified bacterium is able to produce a tripeptide γ-Glu-Val-Gly as described herein.

The bacterium as described herein has been modified to harbor a. gene encoding a protein having L-threonine 3-dehydrogenase activity and a gene encoding a protein having 2-amino-3-oxobutanoate coenzyme A ligase activity. The gene encoding a protein having L-threonine 3-dehydrogenase activity and the gene encoding a protein having 2-amino-3-oxobutanoate coenzyme A ligase activity can be overexpressed in the bacterium in such a way that the genes are present on different nucleic acid molecules. Alternatively, the genes can be introduced into the bacterium in such a way that the genes are present on one nucleic acid molecule. For example, the gene encoding a protein having L-threonine 3-dehydrogenase activity and the gene encoding a protein having an activity of 2-amino-3-oxobutanoate coenzyme A ligase may be present on one expression vector or on the chromosome. Alternatively, the genes may be present on two different expression vectors. Also, alternatively, a gene may be present on one expression vector and another gene may be present on the chromosome.

As a bacterium belonging to the family Enterobacteriaceae can be an example of the bacterium as described herein, the methods for overexpression of a gene encoding a protein having L-threonine 3-dehydrogenase activity and a gene encoding a protein having 2-amino-3-oxobutanoate coenzyme A ligase activity in a bacterium belonging to the family Enterobacteriaceae are described hereinafter.

A method for the overexpression of a gene encoding a protein having L-threonine 3-dehydrogenase activity and a gene encoding a protein having 2-amino-3-oxobutanoate coenzyme A ligase activity in an Enterobacteriaceae bacterium can be introducing a nucleic acid (DNA) having the gene(s) into the Enterobacteriaceae bacterium. Methods for introducing a nucleic acid such as, for example, a gene, a vector, and the like, into an Enterobacteriaceae bacterium can include, but are not limited to, genetic engineering methods known to the person of ordinary skill in the art, and these are not particularly limited. In the bacterium as described herein, the gene encoding a protein having L-threonine 3-dehydrogenase activity and the gene encoding a protein having 2-amino-3-oxobutanoate coenzyme A ligase activity can be present on a vector that autonomously replicates outside of the chromosome such as a plasmid, or may be incorporated into the chromosome. In addition, as described above, to construct the bacterium as described herein, introduction of the gene encoding a protein having L-threonine 3-dehydrogenase activity and the gene encoding a protein having 2-amino-3-oxobutanoate coenzyme A ligase activity, and impartation or enhancement of the ability to produce a tripeptide γ-Glu-Val-Gly can be performed in any order.

The other methods which can be used to enhance expression of a gene encoding a protein having L-threonine 3-dehydrogenase activity and a gene encoding a protein having 2-amino-3-oxobutanoate coenzyme A ligase activity can include increasing the expression level of the genes by modification of expression regulatory region(s) of these genes. Expression regulatory region(s) of genes can be modified by, for example, replacing the native expression regulatory region(s) of these genes with native and/or modified foreign regulatory region(s). The phrase "an expression regulatory region" can also be referred to as "an expression regulatory sequence". When the genes encoding a protein having L-threonine 3-dehydrogenase activity and/or a protein having 2-amino-3-oxobutanoate coenzyme A ligase activity are organized in an operon structure, the method which can be used to enhance expression of the genes also can include increasing the expression level of the operon having these genes by modification of expression regulatory region(s) of the operon, wherein the modification can be carried out by, for example, replacing the native expression regulatory region(s) of the operon with native and/or modified foreign regulatory region(s). In this method, the expression of one or more genes in the operon, including the gene encoding a protein having L-threonine 3-dehydrogenase activity and the gene encoding a protein having 2-amino-3-oxobutanoate coenzyme A ligase activity, can be enhanced at the same time.

Expression regulatory regions can be exemplified by promoters, enhancers, attenuators and termination signals, anti-termination signals, ribosome-binding sites (RBS) and other expression control elements, such as regions to which repressors or inducers bind and/or binding sites for transcriptional and translational regulatory proteins, for example, in the transcribed mRNA. Such regulatory regions are described, for example, in Sambrook J., Fritsch E. F. and Maniatis T., "Molecular Cloning: A Laboratory Manual", 2nd ed., Cold Spring Harbor Laboratory Press (1989). Modification of expression regulatory region(s) of a gene can be combined with increasing the copy number of the gene (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters suitable for enhancing expression of a gene encoding a protein having L-threonine 3-dehydrogenase activity and a gene encoding a protein having 2-amino-3-oxobutanoate coenzyme. A ligase activity can be the potent promoters that are stronger than the native promoters of the genes. For example, the lac promoter, the trp promoter, the trc promoter, the tac promoter, tet promoter, araBAD promoter, rpoH promoter, msrA promoter, Pml promoter (derived from the genus *Bifidobacterium*), and the $P_R$ and $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of a gene to obtain a stronger promoter function, thus resulting in the increased transcription level of the gene located downstream from the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

The copy number of a gene or the presence or absence of a gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion ligation and transformation of DNA, selection of an oligonucleotide as a primer, incorporation of mutations, and the like may be ordinary methods well-known to the persons of ordinary skill in the art. These methods are described, for example, in Sambrook J., Fritsch E. F. and Maniatis T., "Molecular Cloning: A Laboratory Manual", 2nd ed., Cold Spring Harbor Laboratory Press (1989) or Green M. R. and Sambrook J. R., "Molecular Cloning: A Laboratory Manual", 4th ed., Cold Spring Harbor Laboratory Press (2012); Bernard R. Glick, Jack J. Pasternak and Cheryl L. Patten, "Molecular Biotechnology: principles and applications of recombinant DNA", 4th ed., Washington, D.C., ASM Press (2009).

Any methods for manipulation with recombinant DNA can be used including conventional methods such as, for example, transformation, transfection, infection, conjugation, and mobilization. Transformation, transfection, infection, conjugation or mobilization of a bacterium with the DNA encoding a protein can impart to the bacterium the ability to synthesize the protein encoded by the DNA. Methods of transformation, transfection, infection, conjugation, and mobilization include any known methods. For example, a method of treating recipient cells with calcium chloride so as to increase permeability of the cells of *E. coli* K-12 to DNA has been reported for efficient DNA transformation and transfection (Mandel M. and Higa A., Calcium-dependent bacteriophage DNA infection, *J. Mol. Biol.,* 1970, 53:159-162). Methods of specialized and/or generalized transduction have been described (Morse M. L. et al., Transduction in *Escherichia coli* K-12, *Genetics,* 1956, 41(1):142-156; Miller J. H., *Experiments in Molecular Genetics,* Cold Spring Harbor, N.Y.: Cold Spring Harbor La. Press, 1972). Other methods for random and/or targeted integration of DNA into the host microorganism can be applied, for example, "Mu-driven integration/amplification" (Akhverdyan et al., *Appl. Microbiol. Biotechnol.,* 2011, 91:857-871), "Red/ET-driven integration" or "λRed/ET-mediated integration" (Datsenko K. A. and Wanner B. L., *Proc. Natl. Acad. Sci. USA* 2000, 97(12):6640-45; Zhang Y., et al., *Nature Genet.,* 1998, 20:123-128). Moreover, to insert multiple desired genes in addition to Mu-driven replicative transposition (Akhverdyan et al., *Appl. Microbiol. Biotechnol.,* 2011, 91:857-871), and chemically induce chromosomal evolution based on recA-dependent homologous recombination resulting in an amplification of the desired genes (Tyo K. E. J. et al., *Nature Biotechnol.,* 2009, 27:760-765), methods can be used which utilize different combinations of transposition, site-specific and/or homologous Red/ET-mediated recombinations, and/or P1-mediated generalized transduction (see, for example, Minaeva N. et al., *BMC Biotechnology,* 2008, 8:63; Koma D. et al., *Appl. Microbiol. Biotechnol.,* 2012, 93(2):815-829).

Methods for overexpression of a gene encoding a protein having L-threonine 3-dehydrogenase activity and a gene encoding a protein having 2-amino-3-oxobutanoate coenzyme A ligase activity in bacterial species other than a bacterium belonging to the family Enterobacteriaceae can be applied mutatis mutandis by referring to the methods described herein for the bacterium belonging to the family Enterobacteriaceae, or those methods can be used that are known to the persons of ordinary skill in the art. Furthermore, it is within the ordinary skill to use common methods that are suitable for gene overexpression in a bacterium belonging to the family Enterobacteriaceae. Moreover, the methods suitable for the gene overexpression in an Enterobacteriaceae bacterium can be appropriately modified and used to overexpress a gene in other species of bacteria, and contrariwise. Therefore, the methods for gene overexpression described herein may, virtually, be applied to any bacterium as described herein.

Hereinafter, variants of the gene encoding a protein having L-threonine 3-dehydrogenase activity and variants of the protein having L-threonine 3-dehydrogenase activity, specifically variants of those native to *E. coli* will be described. The below descriptions of such variants of the gene and protein can also be applied mutatis mutandis to any gene and protein, including a gene native to a bacterial species other than *E. coli* and encoding a protein having L-threonine 3-dehydrogenase activity and the encoded protein, and a gene encoding a protein having 2-amino-3-oxobutanoate coenzyme A ligase activity and the encoded protein.

There may be differences in DNA sequences between the bacterial families, genera, species or strains. Therefore, the gene encoding a protein having L-threonine 3-dehydrogenase activity is not limited to the gene having the nucleotide sequence shown in SEQ ID NO: 1, but may include genes each of which has a variant nucleotide sequence of SEQ ID NO: 1 and encodes a protein having L-threonine 3-dehydrogenase activity. Similarly, the protein having L-threonine 3-dehydrogenase activity is not limited to the protein having the amino acid sequence shown in SEQ ID NO: 2, but may include proteins each of which has a variant amino acid sequence of SEQ ID NO: 2 and has L-threonine 3-dehydrogenase activity. Examples of such variant nucleotide sequence or variant amino acid sequence may include homologues of and artificially modified ones of the gene encoding a protein having L-threonine 3-dehydrogenase activity exemplified above or of the protein having L-threonine 3-dehydrogenase activity exemplified above.

The phrase "a variant protein" can mean a protein which has a valiant amino acid sequence of SEQ ID NO: 2.

The phrase "a variant protein" can specifically mean a protein which has one or more imitations in the sequence as compared with the amino acid sequence shown in SEQ ID NO: 2, whether they are substitutions, deletions, insertions, and/or additions of one or several amino acid residues, but which still maintains the L-threonine 3-dehydrogenase activity as described herein, or of which the three-dimensional structure is not significantly changed relative to the non-modified protein such as, for example, the protein having the amino acid sequence shown in SEQ ID NO: 2. The number of changes in the variant protein depends on the position of amino acid residue(s) in the three-dimensional structure of the protein or the type of amino acid residue(s). It can be, but is not strictly limited to, 1 to 50, in another example 1 to 30, in another example 1 to 15, in another example 1 to 10, and in another example 1 to 5, in SEQ NO: 2. This is possible because amino acids can have high homology to one another, so that the activity of a protein is not affected by a change between such amino acids, or the three-dimensional structure of a protein is not significantly changed relative to the corresponding non-modified protein by a change between such amino acids. Therefore, the variant protein may be a protein having an amino acid sequence having a homology, defined as the parameter "identity" when using the computer program BLAST, of not less than 60%, of not less than 65%, not less than 70%, not less than 75%, not less than 80%, not less than 85%, not less than 90%, not less than 95%, not less than 98%, or not less than 99% with respect to the entire amino acid sequence shown in SEQ ID NO: 2, as long as the L-threonine 3-dehydrogenase activity of the protein is maintained, or the three-dimensional structure of the protein is not significantly changed relative to the non-modified protein such as, for example, the protein having the amino acid sequence shown in SEQ ID NO: 2.

The exemplary substitution, deletion, insertion, and/or addition of one or several amino acid residues can be a conservative mutation(s). The representative conservative mutation can be a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Set or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The exemplary substitution, deletion, insertion, and/or addition of one or several amino acid residues can also be a non-conservative mutation(s) provided that the mutation(s) is/are compensated by one or more secondary mutation(s) in a different position(s) of amino acids sequence so that the L-threonine 3-dehydrogenase activity of the variant protein is maintained, or the three-dimensional structure of the protein is not significantly changed relative to the non-modified protein such as, for example, the protein having the amino acid sequence shown in SEQ ID NO: 2.

To evaluate the degree of protein or DNA homology, several calculation methods can be used, such as a BLAST search, FASTA search and ClustalW method. The BLAST (Basic Local Alignment Search Tool) search is the heuristic search algorithm employed by the programs blastp, blastn, blastx, megablast, tblastn, and tblastx; these programs ascribe significance to their findings using the statistical methods of Karlin S. and Altschul S. F. ("Methods for assessing the statistical significance of molecular sequence features by using general scoring schemes" Proc. Natl. Acad. Sci. USA, 1990, 87:2264-2268; "Applications and statistics for multiple high-scoring segments in molecular sequences". *Proc. Natl. Acad. Sci. USA,* 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.,* 1990, 183:63-98). The ClustalW method is described by Thompson J.D. et al. ("CLUSTAL W: improving the sensitivity of progressive multiple sequence alignment through sequence weighting, position-specific gap penalties and weight matrix choice", *Nucleic Acids Res.,* 1994, 22:4673-4680). In this specification, the phrase "homology" may mean "identity", which is the identity of amino acid sequences or nucleotide sequences. The sequence identity between two sequences is calculated as the ratio of residues matching in the two sequences when aligning the two sequences so as to achieve a maximum alignment with each other. The phrase "identity" between amino acid sequences may specifically mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The phrase "identity" between nucleotide sequences may specifically mean an identity calculated by blastn with default scoring parameters (i.e. Match/Mismatch Scores=1, −2; Gap Costs=Linear), unless otherwise stated.

The phrase "a variant nucleotide sequence" can mean a nucleotide sequence which encodes a protein having L-threonine 3-dehydrogenase activity, such as the protein having the amino acid sequence shown in SEQ ID NO: 2, using any synonymous amino acid codons according to the standard genetic code table (see, e.g., Lewin B., "Genes VIII", 2004, Pearson Education, Inc., Upper Saddle River, NJ 07458). Therefore, the gene encoding a protein having L-threonine 3-dehydrogenase activity can be a gene having a variant nucleotide sequence due to the degeneracy of the genetic code.

The phrase "a variant nucleotide sequence" can also mean a nucleotide sequence that is able to hybridize under stringent conditions with a nucleotide sequence complementary to the sequence shown in SEQ ID NO: 1 or a probe that can be prepared from the nucleotide sequence provided that it encodes a protein having L-threonine 3-dehydrogenase activity. The phrase "stringent conditions" can include conditions under which a specific hybrid, for example, a hybrid having homology, defined as the parameter "identity" when using the computer program BLAST, of not less than 60%, not less than 65% not less than 70%, not less than 75%, not less than 80%, not less than 85%, not less than 90%, not less than 95%, not less than 96%, not less than 97%, not less than 98%, or not less than 99%, is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate) at 60° C., 0.1×SSC, 0.1% SDS at 60° C. or 0.1×SSC, 0.1% SDS at 65° C. The duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR (polymerase chain reaction; refer to White T. J. et al., The polymerase chain reaction, *Trends Genet.,* 1989, 5:185-189) using oligonucleotides as primers prepared on the basis of the sequence shown in SEQ ID NO: 1 and a DNA fragment containing the nucleotide sequence to be used as the probe as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after the hybridization can be, for example, 2×SSC, 0.1% SDS at 50° C., 60° C. or 65° C.

The phrase "a variant nucleotide sequence" can also mean a nucleotide sequence that encodes a variant protein.

Since the gene encoding a protein having L-threonine 3-dehydrogenase activity and native to *E. coli* has already been elucidated (see above), the gene encoding a protein having L-threonine 3-dehydrogenase activity and native to *E. coli* or a variant nucleotide sequence thereof can be obtained by cloning from *E. coli* by PCR utilizing DNA of *E. coli* and oligonucleotide primers prepared based on the nucleotide sequence of the tdh gene native to *E. coli*; or a mutagenesis method of treating a DNA containing the tdh gene, in vitro, for example, with hydroxylamine, or a mutagenesis method of treating *E. coli* harboring the tdh gene with ultraviolet (UV) irradiation or a mutating agent such as N-methyl-N'-nitro-N-nitrosoguanidine (NTG) and nitrous acid usually used for the such treatment; or chemical synthesis as a full-length gene structure. Genes encoding the proteins having, L-threonine 3-dehydrogenase activity native to other organism such as a bacterium of the family Enterobacteriaceae other than *E. coli* or a variant nucleotide sequence thereof can be obtained in a similar manner.

The phrase "non-modified", which can be equivalent to the phrase "native", "natural", or "wild-type", in reference to a gene (for example, "a non-modified gene") and a protein (for example, "a non-modified protein"), can mean, respectively, a native gene and a native protein that exist naturally in, are expressed naturally in, and/or are produced naturally by an organism, specifically a non-modified strain of a bacterium, for example, a wild-type strain of a bacterium of the family Enterobacteriaceae such as, for example, the *E. coli* MG1655 strain (ATCC 47076), the *E. coli* W3110 strain (ATCC 27325), the *P. ananatis* AJ13355 strain (FERM BP-6614), and so forth. A non-modified gene can encode a non-modified protein.

The phrase "native to" in reference to a protein or a nucleic acid native to a particular species of organisms such as, for example, a bacterial species, can refer to a protein or a nucleic acid that is native to that species. That is, a protein or a nucleic acid native to a particular species can mean the protein or the nucleic acid, respectively, that exists naturally in that species. A protein or a nucleic acid native to a particular species can be isolated from that species and sequenced using means known to the one of ordinary skill in the art. Moreover, as the amino acid sequence or the nucleotide sequence of a protein or nucleic acid, respectively, isolated from a species in which the protein or nucleic acid exists, can easy be determined, the phrase "native to" in reference to a protein or a nucleic acid can also refer to a protein or a nucleic acid that can be obtained using any means, for example, using a genetic engineering technique, including recombinant DNA technology, or a chemical synthesis method, or the like, so long as the amino acid sequence of the protein or the nucleotide sequence of the nucleic acid thus obtained is identical to the amino acid sequence of the protein or the nucleotide sequence of the nucleic acid that exists naturally in the species. The phrase "a protein" can include, but are not limited to, peptides, oligopeptides, polypeptides, proteins, enzymes, and so forth. The phrase "a nucleic acid" can include deoxyribonucleic acid (DNA) and ribonucleic acid (RNA), and can specifically include, but are not limited to, regulatory sequences, including promoters, attenuators, terminators, and the like, genes, intergenic sequences, sequences encoding signal peptides, pro-moieties of proteins, artificial amino acid sequences, and so forth. Specific examples of amino acid sequences and nucleotide sequences, and homologues thereof native to various species are described herein. Specific examples of proteins native to *E. coli* include TDH and KBL having the amino acid sequences shown in SEQ ID NOs: 2 and 4, respectively. Specific examples of genes native to *E. coli* include tdh and kbl genes having the nucleotide sequences shown in SEQ ID NOs: 1 and 3, respectively.

There are other genes the expression of which can be altered by either down-regulating the expression (i.e. attenuating the expression) or overexpressing the gene, and such alteration(s) can have a positive effect on the production of the tripeptide γ-Glu-Val-Gly during cultivation of the bacterium as described herein. The bacterium may have been modified to have such alteration(s). The bacterium may have been specifically modified to have any one of or any combination of such alteration(s).

The phrase "a bacterium has been modified to attenuate the expression a gene" can mean that the bacterium has been modified in such a way that in the modified bacterium the total activity of the corresponding gene product is decreased, or the expression level (i.e. expression amount) of the gene is decreased, as compared with a non-modified strain. The bacterium may be modified so that the activity of a protein encoded by an objective gene per cell is decreased to, for example, 50% or less, 20% or less, 10% or less, 5% or less, or 0%, of the activity of the protein in a non-modified strain.

The bacterium may be modified so that the expression level of an objective gene per cell is decreased to, for example, 50% or less, 20% or less, 10% or less, 5% or less, or 0%, of the expression level of the gene in a non-modified strain.

The aforementioned description concerning overexpression of a gene encoding a protein having L-threonine 3-dehydrogenase activity and a gene encoding a protein having 2-amino-3-oxobutanoate coenzyme A ligase activity can be applied mutatis mutandis to other genes.

Specific methods for attenuating the expression of gene(s) or overexpressing gene(s) are well known to persons of ordinary skill in the art. Attenuation of the expression of a gene can be attained by, for example, disrupting or deleting the gene. Overexpression of a gene can be attained by, for example, a similar manner as that for overexpression of a gene encoding a protein having L-threonine 3-dehydrogenase activity and a gene encoding a protein having 2-amino-3-oxobutanoate coenzyme A ligase activity.

Examples of such alterations can include attenuating the expression of genes encoding enzymes that prevent glycine degradation and enzymes that increase glutamic acid biosynthesis. These alterations can include attenuating the expression of a gcvP gene and attenuating the expression of sucAB operon genes. The gcvP gene encodes a component of the glycine cleavage system, which prevents glycine degradation due to a glycine decarboxylase reaction (Yishai et al., ACS Synth Biol. 2017; 6(9):1722-1731). The sucAB genes encode two subunits of 2-ketoglutarate dehydrogenase (KGDH). Attenuation of the expression of the sucAB genes, such as decrease in the activity of proteins encoded by the genes, can result in a decrease in KGDH activity. For example, it has been reported that attenuation of the expression of the sucAB genes results in decreasing KGDH activity by 60%, thereby elevating glutamic acid accumulation 3-fold (U.S. Pat. No. 7,604,979 B2). A decrease in KGDH activity is useful for γ-Glu-Val-Gly production due to its positive influence on glutamic acid synthesis.

Examples of such alterations can also include overexpression of genes encoding proteins involved in the production of L-valine and proteins involved in export of the tripeptide γ-Glu-Val-Gly. These alterations can include overexpression of ilvGMEDA operon genes (U.S. Pat. No. 5,998,178 A) and the tolC gene. The tolC gene encodes an outer membrane protein involved in a range of tripartite efflux complexes (Benz R. et al., TolC of *Escherichia coli* functions as an outer membrane channel, *Zentralbl. Bakteriol.*, 1993, 278 (2-3):187-196). The ilvGMEDA operon can include an ilvG gene having a mutation that results in regeneration of the activity of acetohydroxylic acid synthase II (AHAS II) encoded by the ilvG gene (Russian Patent No. 2212447 C2; U.S. Pat. No. 9,896,704 B2).

The bacterium can have, in addition to the properties already mentioned, other specific properties such as various nutrient requirements, drug resistance, drug sensitivity, and drug dependence, without departing from the scope of the present invention.

2. Method

The method of producing a tripeptide γ-Glu-Val-Gly using a bacterium as described herein includes the steps of cultivating (also called culturing) the bacterium in a culture medium to allow γ-Glu-Val-Gly to be produced, excreted or secreted, and/or accumulated in the culture medium or in the bacterial cells, or both, and collecting the γ-Glu-Val-Gly from the culture medium and/or the bacterial cells. The method may include, optionally, the step of purifying a target tripeptide γ-Glu-Val-Gly from the culture medium and/or the bacterial cells. The γ-Glu-Val-Gly can be produced in such a loan as described above. The γ-Glu-Val-Gly can be produced particularly in a free form or as a salt thereof, or as a mixture of them. For example, sodium, potassium, ammonium, and the like salts can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to persons of ordinary skill in the art.

The cultivation of the bacterium, and collection, and, optionally, purification of a tripeptide γ-Glu-Val-Gly from the medium and the like may be performed in a manner similar to the conventional fermentation methods wherein an L-amino acid is produced using a microorganism. The culture medium can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under conditions suitable for cultivating the chosen bacterium in the method for producing a tripeptide γ-Glu-Val-Gly. For example, the cultivation can be performed under aerobic conditions for from 16 to 72 hours or for from 32 to 4 hours, the culture temperature during cultivation can be controlled within from 30 to 45° C. or within from 30 to 37° C., and the pH can be adjusted between 5 and 8 or between 6 and 7.5. The pH can be adjusted using an inorganic or organic acidic or alkaline substance such as urea, calcium carbonate or ammonia gas.

After cultivation, the tripeptide γ-Glu-Val-Gly can be collected from the culture medium. Specifically, the tripeptide γ-Glu-Val-Gly present outside of cells can be collected from the culture medium. Also, after cultivation, the tripeptide γ-Glu-Val-Gly can be collected from the bacterial cells, specifically, the cells can be disrupted, a supernatant can be obtained by removing solids such as the cells and the cell-disrupted suspension (so-called cell debris), and then the tripeptide γ-Glu-Val-Gly can be collected from the supernatant. Disruption of the cells can be performed using, for example, methods that are well-known in the art, such as ultrasonic lysis using high frequency sound waves, or the like. Removal of solids can be performed by, for example, centrifugation or membrane filtration. Collection of the tripeptide γ-Glu-Val-Gly from the culture medium or the supernatant etc can be performed using, for example, conventional techniques such as concentration, crystallization, ion-exchange chromatography, medium or high pressure liquid chromatography, or a combination of these.

EXAMPLES

The present invention will be more specifically explained with reference to the following non-limiting examples.

Example 1

Construction of the *E. Coli* γ-EVG-Producing Strain

The *E. coli* strain MG1655 $P_L$-ilvG*MEDA ΔicdC:: $P_{tac4071}$φ10-gshA50 attB φ80::KmR-$P_{tac4071}$φ10-gshB$^{M165F}$ (LI029-1) was constructed as a model γ-EVG-producing strain. For that purpose, the strain MG1655 ilvG*MEDA ilvH** was used as a starting material. The strain MG1655 ilvG*MEDA ilvH** can be constructed from the *E. coli* strain K-12 substr. MG1655 (ATCC 47076) using conventional recombinant methods and/or a genes chemical synthesis method. The strain MG1655 ilvG*MEDA ilvH** has a mutation in the ilvG gene (specifically, ilvG$_5$ mutation, which is the insertion of two base pairs (AA) at 981 position from the start of the gene, upstream of the sequence TGACTGGCA) that restores the frame-shift in the wild-type ilvG gene (specifically, the wild-type protein sequence . . . PLNQ& is replaced with . . . PLNQNDW . . . ), resulting in the restoration of acetohydroxyacid synthase II (AHAS II) activity (Russian Patent No. 2212447 C2; U.S. Pat. No. 9,896,704 B2), and also instills two mutations in ilvH gene that results in the replacement of $^{17}$Ser with Phe and $^{14}$Gly with Asp in the small subunit of acetolactate synthase III (AHAS III) (U.S. Pat. No. 6,737,255 B2). To overproduce valine in strain MG1655 ilvG*MEDA ilvH**, the native ilvG*MEDA operon was replaced with an artificial regulator region, which contains the phage lambda $P_L$ promoter linked to the modified Shine-Dalgarno sequence SD1 (SD sequence from pET22 plasmid), by the method developed by Datsenko and Wanner (Datsenko K. A. and Wanner B. L., Proc. Natl. Acad. Sci. USA, 2000, 97:12:6640-45) called "λRed-dependent integration". According to this procedure, the PCR primers P1 (SEQ ID NO: 5) and P2 (SEQ ID NO: 6) were constructed. Oligonucleotide P1 (SEQ ID NO: 5) is homologous to the region upstream of the ilvG gene and the region adjacent to the chloramphenicol resistance gene (cat), which was obtained from the chromosomal DNA of BW25113 cat-$P_L$-yddG. Obtaining BW25113 cat-$P_L$-yddG is described in detail (EP1449918A1, Russian patent RU2222596 C1). BW25113 cat-$P_L$-yddG strain was used as a template for PCR. Oligonucleotide P2 (SEQ ID NO: 6) is homologous to both the ilvG region and the region downstream of the $P_L$ promoter, which was obtained from the template chromosome and contains the SD1 sequence. Conditions for PCR were as follows: denaturation for 3 min at 95° C.; profile for two first cycles: 1 min at 95° C., 30 sec at 34° C., 80 sec at 72° C.; profile for the last 30 cycles: 30 sec at 95° C., 30 sec at 50° C., 80 sec at 72° C.; final step: 5 min at 72° C. The resulting DNA fragment (1957 bp) (SEQ ID NO: 7) was purified in an agarose gel and used for electroporation of the *E. coli* strain MG1655 containing the helper plasmid pKD46 with a temperature-sensitive replicon. The plasmid pKD46 (Datsenko, K. A. and Wanner, B. L., Proc. Natl. Acad. Sci. USA, 2000, 97 (12):6640-45) includes a 2,154 nt (31088-33241) DNA fragment from phage λ (GenBank, accession No. J02459) and contains the genes of the λRed homologous recombination system (gamma, beta, exo genes) under the control of the arabinose-inducible $P_{araB}$ promoter. The plasmid pKD46 is necessary to integrate the DNA fragment into the bacterial chromosome.

Electrocompetent cells were prepared as follows: *E. coli* strain MG1655 was grown overnight at 30° C. in LB medium (Sambrook, J. and Russell, D. W., "Molecular Cloning: A Laboratory Manual", $3^{rd}$ ed., Cold Spring Harbor Laboratory Press (2001)) containing ampicillin (100 mg/L), and the culture was diluted in 100 times with 5 mL of SOB medium (Sambrook, J. Fritsch, E. F. and Maniatis, T., "Molecular Cloning: A Laboratory Manual", $2^{nd}$ ed., Cold Spring Harbor Laboratory Press (1989)) with ampicillin (100 mg/L) and L-arabinose (1 mM). The cells were grown with aeration (250 rpm) at 30° C. to an $OD_{600}$ of about 0.6 and then made electrocompetent by concentrating 100-fold and washing three times with ice-cold deionized $H_2O$. Electroporation was performed using 200 µl of cells and about 100 ng of DNA fragment (SEQ ID NO: 7). Then, cells were incubated with 1 mL of SOC medium (Sambrook, J., Fritsch, E. F. and Maniatis, T., "Molecular Cloning: A Laboratory Manual", $2^{nd}$ ed., Cold Spring Harbor Laboratory Press (1989)) at 37° C. for 2.5 h, placed onto plates containing LB-medium, agar (1.5%) and chloramphenicol (20 µg/mL), and grown at 37° C. to select chloramphenicol resistant ($Cm^R$)-recombinants. Then, to eliminate the pKD46 plasmid, one passage on L-agar with Cm (20 µg/mL) at 42° C. was performed, and the resulting individual colonies were tested for sensitivity to ampicillin. Thus, the strain MG1655 cat-$P_{L-SD1}$-ilvG*MEDA was obtained.

The replacement of the native regulatory region of ilvG*MEDA operon with the $P_{L-SD1}$ promoter marked with the chloramphenicol resistance gene was confirmed by PCR using locus-specific primers P3 (SEQ ID NO: 8) and P4 (SEQ ID NO: 9). Conditions for PCR verification were as follows: denaturation for 3 mm at 95° C.; profile for the 25 cycles: 30 sec at 95° C., 30 sec at 59° C., 1 min at 72° C.; final step: 7 min at 72° C. DNA fragment, obtained in the reaction with the cells of MG1655 strain as a template, was 566 bp in length (SEQ ID NO: 10). DNA fragment, obtained in the reaction with the cells of MG1655 cat-$P_{L-SD1}$-ilvG*MEDA strain as a template, was 2055 bp in length (SEQ ID NO: 11). To eliminate $Cm^R$ marker from the strain MG1655 cat-$P_{L-SD1}$-ilvG*MEDA, cells were transformed with the plasmid pMW118-int-xis ($Ap^R$) (WO2005/010175). $Ap^R$ clones were grown on LB-agar plates containing 150 mg/L ampicillin at 30° C. Several tens of $Ap^R$ clones were picked up and tested for chloramphenicol sensitivity. The plasmid pMW118-int-xis was eliminated from $Cm^S$ cells by incubation on LB agar plates at 42° C. Thus, the strain MG1655 $P_{L-SD1}$-ilvG*MEDA was obtained.

γ-Glutamate-cysteine ligase (GshA) catalyzes the first step of γ-EVG biosynthesis. To increase expression of the gshA gene encoding GshA, the expression cassette ΔicdC::KmR-$P_{tac4071\phi10}$-gshA50 (gshA50 means Gsh$A^{L135F/Q114A}$, US2016326510 A1) was introduced into strain MG1655 $P_{L-SD1}$-ilvG*MEDA by P1-transduction (Sambrook et al, "Molecular Cloning A Laboratory Manual, 2nd Edition", Cold Spring Harbor Laboratory Press (1989)). Construction of the expression cassette ΔicdC::KmR-$P_{tac4071\phi10}$-gshA50 is described in the Reference example 3. Kanamycin-resistant transductants were selected and verified by PCR with the locus-specific primers P5 (SEQ ID NO: 12) and P6 (SEQ ID NO: 13). Conditions for PCR verification were as follows: denaturation step for 3 min at 95° C.; profile for 25 cycles: 30 sec at 95° C., 30 sec at 55° C., 1 min at 72° C.; final step: 7 min at 72° C. There was no DNA fragment in the reaction with the cells of parental strain MG1655 $P_{L-SD1}$-ilvG*MEDA as a template. The DNA fragment (SEQ ID NO: 14) obtained in the reaction when using the MG1655 $P_{L-SD1}$-ilvG*MEDA ΔicdC::$P_{tac4071\phi10}$-gshA50 strain as a template, was 1850 nt in length. The kanamycin resistance (KmR) marker was eliminated from MG1655 $P_{L-SD1}$-ilvG*MEDA ΔicdC::KmR-$P_{tac4071\phi10}$-gshA50 as described above. As a result, the strain MG1655 $P_{L-SD1}$-ilvG*MEDA ΔicdC:$P_{tac4071\phi10}$-gshA50 was obtained.

Glutathione synthetase (GshB) catalyzes the second step of γ-EVG biosynthesis. To overexpress glutathione synthetase, the cassette attB φ80::KmR-$P_{tac4071\phi10}$-gshB$^{M165F}$ encoding mutant glutathione (γ-EVG) synthetase with improved selectivity to γ-EV substrate (Reference example 4) was introduced into strain MG1655 $P_{L-SD1}$-ilvG*MEDA ΔicdC::$P_{tac4071\phi10}$-gshA50 by P1-transduction. The donor strain MG1655 attB φ80::KmR-$P_{tac4071\phi10}$-gshB$^{M165F}$ can be constructed as described in detail in Reference Example 1. KmR transductants were selected and verified by means of PCR with locus-specific primers P7 (SEQ ID NO: 33) and P8 (SEQ ID NO: 34). Conditions for PCR verification were as follows: denaturation step for 3 min at 95° C.; profile for the 25 cycles: 30 sec at 95° C., 30 sec at 61° C., 1 min at 72° C.; final step: 7 min at 72° C. There was no DNA fragment in the reaction with the parental strain MG1655 $P_{L-SD1}$-ilvG*MEDA ΔicdC::$P_{tac4071\phi10}$-gshA50 as a template. DNA fragment (SEQ ID NO: 36), obtained in the reaction with the cells of MG1655 $P_{L-SD1}$-ilvG*MEDA ΔicdC:$P_{tac4071\phi10}$-gshA50 attB phi80::KmR-Ptac4071φ10-gshB*M165F strain as a template, was 1917 nt in length. As a result, the strain MG1655 $P_L$-ilvG*MEDA ΔicdC::$P_{tac4071\phi10}$-gshA50 attB φ80::KmR-$P_{tac4071\phi10}$-gshB$^{M165F}$ (L1029-1) was obtained.

Example 2

Positive Effect of the kbl-tdh Operon Overexpression on γ-EVG Production

To provide γ-EVG precursors, the regulator region of the kbl-tdh operon was modified, namely the native promoter region of the kbl-tdh operon was replaced with the $P_L$ promoter from phage λ, by the method of Red-dependent integration (Datsenko, K. A. and Wanner, B. L., Proc. Natl. Acad. Sci. USA, 2000, 97 (12):6640-45) described above. According to this procedure, the PCR primers P9 (SEQ ID NO: 15) and P10 (SEQ ID NO: 16) were constructed. Oligonucleotide P9 (SEQ ID NO: 15) is homologous to the region upstream of the kbl gene and the region adjacent to the chloramphenicol resistance gene in the chromosomal DNA of the MG1655 cat-$P_{L-SD1}$-ilvG*MEDA strain (Example 1), which was used as a template for PCR. Oligonucleotide P10 (SEQ ID NO: 16) is homologous to both the kbl region and the region downstream to the $P_L$ promoter in the chromosome of the MG1655 cat-$P_{L-SD1}$-ilvG*MEDA strain. Conditions for PCR were as follows: denaturation for 3 min at 95° C.; profile for two first cycles: 1 min at 95° C., 30 sec at 34° C., 80 sec at 72° C.; profile for the last 30 cycles: 30 sec at 95° C., 30 sec at 50° C., 80 sec at 72° C.;

final step: 5 min at 72° C. The obtained DNA fragment (1969 bp) (SEQ ID NO: 17) was purified by "Silica Bead DNA Gel Extraction Kit" ("Thermo Scientific"), and used for electroporation of the E. coli strain MG1655 containing the plasmid pKD46. Chloramphenicol resistant recombinants were selected after electroporation. The replacement of the native regulatory region of kbl-tdh operon with the $P_{L-SD1}$ promoter, marked with the Cm resistance gene, was confirmed by PCR using locus-specific primers P11 (SEQ ID NO: 18) and P12 (SEQ ID NO: 19). Conditions for PCR verification were as follows: denaturation for 3 min at 95° C.; profile for the 30 cycles: 30 sec at 95° C., 30 sec at 59° C., 1 min at 72° C.; final step: 7 min at 72° C. The DNA fragment obtained in the reaction with the MG1655 strain as a template was 482 nt in length (SEQ ID NO: 20). The DNA fragment obtained in the reaction with the MG1655 cat-$P_L$-kbl-tdh strain as a template was 2273 nt in length (SEQ ID NO: 21). Thus, the strain MG1655 cat-$P_{L-SD1}$-kbl-tdh was obtained.

Then, the expression cassette cat-$P_{L-SD1}$-kbl-tdh was introduced into the γ-EVG-producing strain MG1655 $P_{L-SD1}$-ilvG*MEDA ΔicdC::$P_{tac4071\varphi10}$-gshA50 attB φ80::KmR-$P_{tac4071\varphi10}$-gshB$^{M165F}$ (L1029-1) by P1-transduction. As a result, the strain MG1655 $P_{L-SD1}$-ilvG*MEDA ΔicdC::$P_{tac4071\varphi10}$-gshA50 attBφ80::KmR-$P_{tac4071\varphi10}$-gshB$^{M165F}$ cat-$P_{L-SD1}$-kbl-tdh (L1031-1) was obtained. Evaluation of the strain L1031-1 in comparison with the parent L1029-1 demonstrated the positive effect of kbl-tdh operon overexpression on γ-EVG synthesis (Table 1), namely, γ-EVG production increased more than 3.5 times and, as expected, production of the byproduct γ-EV was decreased.

C. The obtained DNA fragment (1614 bp) (SEQ ID NO: 24) was purified by "Silica Bead DNA Gel Extraction Kit" ("Thermo Scientific") and used for electroporation of the E. coli strain MG1655, containing the plasmid pKD46. Kanamycin resistant recombinants were selected and the deletion of gcvP gene marked with KmR gene in selected mutants was verified by PCR using locus-specific primers P15 (SEQ ID NO: 25) and P16 (SEQ ID NO: 26). Conditions for PCR verification were as follows: denaturation step for 3 min at 95° C.; profile for the 25 cycles: 30 sec at 95° C., 30 sec at 59° C., 2 min at 72° C.; final step: 7 min at 72° C. The DNA fragment obtained in the reaction with the chromosomal DNA from parental gcvP$^+$ strain MG1655 as a template as 3136 nt in length (SEQ ID NO: 27). The DNA fragment obtained in the reaction with the chromosomal DNA from mutant MG1655 ΔgcvP::KmR strain as a template was 1803 nt in length (SEQ ID NO: 28). As a result, the strain MG1655 ΔgcvP::KmR was obtained. The strain MG1655ΔgcvP::KmR was used as a donor for P1-mediated introduction of deletion of the gcvP gene into the strain MG1655 $P_{L-SD1}$-ilvG*MEDA ΔicdC::$P_{tac4071\varphi10}$-gshA50 attBφ80::$P_{tac4071\varphi10}$-gshB$^{M165F}$ cat-$P_{L-SD1}$-kbl-tdh, which was obtained from the strain L1031-1 by the KmR marker excision. As a result, the strain MG1655 $P_L$-ilvG*MEDA ΔicdC::$P_{tac4071\varphi10}$-gshA50 attB φ80::$P_{tac4071\varphi10}$-gshB$^{M165F}$ cat-$P_{L-SD1}$-kbl-tdh ΔgcvP::KmR (L1033-1) was selected. Evaluation of the strain L1033-1 revealed the positive effect of gcvP gene disruption on γ-EVG production; and as expected, the byproduct γ-EV was decreased (Table 2).

TABLE 1

Effect of kbl-tdh operon overexpression.

| Strain | MG1655 $P_L$-ilvG*MEDA ΔicdC::$P_{tac4071\varphi10}$-gshA50 attB φ80::KmR-$P_{tac4071\varphi10}$-gshB$^{M165F}$ (L1029-1) | L1029-1 cat-$P_{L-SD1}$-kbl-tdh (L1031-1) |
|---|---|---|
| Biomass, g/B | 21 | 20 |
| γ-EVG    g/L | 0.8 | 3.1 |
|          g/B | 0.3 | 1.3 |
| Yield, % | 0.5 | 1.7 |
| γ-EV, g/L | 11.0 | 14.8 |
| γ-EV/γ-EVG, % | 1375 | 478 |

Conditions: fed-batch EVG-cultivation, 24 h; HPLC data (Reference examples 6 and 7).

Example 3

Positive Influence of gcvP Gene Disruption on γ-EVG Production

To prevent glycine degradation due to a glycine decarboxylase reaction, the gcvP gene encoding a component of the glycine cleavage system was deleted by the method of Red-dependent integration described above. According to this procedure, the PCR primers P13 (SEQ ED NO: 22) and P14 (SEQ ID NO: 23) homologous to the both region adjacent to the gcvP gene and gene conferring kanamycin resistance in the template plasmid were constructed. The plasmid pMW118-(λattL-Km-λattR) (EP2100957 A1) was used as a template in PCR reaction. Conditions for PCR were as follows: denaturation step for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final step: 5 min at 72°

TABLE 2

Effect of gcvP gene disruption.

| Strain | MG1655 $P_L$-ilvG*MEDA ΔicdC::$P_{tac4071\varphi10}$-gshA50 attB φ80::KmR-$P_{tac4071\varphi10}$-gshB$^{M165F}$ cat-$P_{L-SD1}$-kbl-tdh (L1031-1) | MG1655 $P_L$-ilvG*MEDA ΔicdC::$P_{tac4071\varphi10}$-gshA50 attB φ80::$P_{tac4071\varphi10}$-gshB$^{M165F}$ cat-$P_{L-SD1}$-kbl-tdh ΔgcvP::KmR (L1033-1) |
|---|---|---|
| Biomass, g/B | 20 | 12 |
| Glucose, g/B | 78 | 43 |
| γ-EVG    g/L | 3.1 | 4.2 |
|          g/B | 1.3 | 1.5 |
| Yield, % | 1.7 | 3.6 |
| γ-EV, g/L | 14.8 | 2.8 |
| γ-EV/γ-EVG, % | 478 | 67 |

Conditions: fed-batch EVG-cultivation, 24 h, HPLC data (Reference examples 6 and 7).

Example 4

Positive Effect of ilvGMEDA Operon Expression on γ-EVG Production

To demonstrate the effect of ilvGMEDA operon expression on γ-EVG production, the expression cassette $P_{L-SD1}$-ilvG*MEDA in the strain MG1655 $P_L$-ilvG*MEDA ΔicdC::$P_{tac4071\varphi10}$-gshA50 attB φ80::$P_{tac4071\varphi10}$-gshB$^{M165F}$ cat-$P_{L-SD1}$-kbl-tdh ΔgcvP:Km (L1033-1) was replaced with the wild-type ilvGMEDA operon. To this end, at first, the strain MG1655 $P_L$-ilvG*MEDA ΔicdC::$P_{tac4071\varphi10}$-gshA50 attB φ80::$P_{tac4071\varphi10}$-gshB$^{M165F}$ $P_{L-SD1}$-kbl-tdh ΔgcvP::KmR (L1034-1) was obtained from the strain L1033-1 by the Cm$^R$ marker elimination. Then, the expression cassette $P_{L-SD1}$-ilvG*MEDA in the strain L1034-1 was replaced with the cassette $P_{L-SD1}$-ilvG*M-ΔilvE::cat-DA by means of P1-transduction. The strain MG1655 $P_{L-SD1}$-ilvG*M-ΔilvE:cat-DA that was used as a donor strain can be constructed as described in detail in Reference example 2. Thus, the strain L1034-1 $P_{L-SD1}$-ilvG*M-ΔilvE::cat-DA that requires isoleucine and valine for growth in minimal medium was obtained.

Then, the expression cassette $P_{L-SD1}$-ilvG*M-ΔilvE::cat-DA in the chromosome of the strain L1034-1 $P_{L-SD1}$-ilvG*M-ΔilvE::cat-DA was replaced with the wild-type ilvGMEDA operon by P1-transduction from *E. coli* strain MG1655; prototrophic transductants were selected in M9 minimal medium. Restoration of the wild-type ilvGMEDA operon in the resulting strain MG1655 ΔicdC::$P_{tac4071φ10}$-gshA50 attB φ80::$P_{tac4071φ10}$-gshB$^{M165F}$ $P_{L-SD1}$-kbl-tdh ΔgcvP::KmR (L1040-1) was confirmed by PCR with locus-specific primers P3 (SEQ ID NO: 8) and P4 (SEQ ID NO: 9). Conditions for PCR verification were as follows: denaturation step for 5 min at 94° C.; profile for the 25 cycles: 30 sec at 94° C., 30 sec at 59° C., 1 min at 72° C.; final step: 7 min at 72° C. DNA fragment, obtained in the reaction with the cells of the parental stairs as a template, was 458 nt in length (SEQ ID NO: 29). The DNA fragment obtained in the reaction with the cells of L1040-1 strain as a template was 566 nt in length (SEQ ID NO: 10). As seen in Table 3, the substitution of the efficient $P_{L-SD1}$-ilvGMEDA expression cassette with the wild-type ilvGMEDA operon into the chromosome of L1040-1 strain resulted in significantly decreasing γ-EVG production as compared to L1034-1.

TABLE 3

Effect of ilvGMEDA operon overexpression.

| Strain | MG1655 $P_L$-ilvG*MEDA ΔicdC::$P_{tac4071φ10}$-gshA50 attB φ80::$P_{tac4071φ10}$-gshB$^{M165F}$ $P_{L-SD1}$-kbl-tdh ΔgcvP::KmR (L1034-1) | MG1655 ΔicdC::$P_{tac4071φ10}$-gshA50 attB φ80::$P_{tac4071φ10}$-gshB$^{M165F}$ $P_{L-SD1}$-kbl-tdh ΔgcvP::KmR (L1040-1) |
|---|---|---|
| γ-EVG, g/L | 3.3 | 1.5 |
| Yield, % | 3.9 | 1.3 |
| γ-EV, g/L | 1.8 | 0.3 |
| γ-EV/γ-EVG, % | 54.8 | 14.8 |

Conditions: fed-batch EVG-cultivation, 24 h, HPLC data (Reference examples 6 and 7).

Example 5

Positive Effect of sucAB Expression on γ-EVG Production

The decrease in 2-ketoglutarate dehydrogenase (KGDH) activity was supposed to be useful for γ-EVG production due to its positive influence on Glu synthesis. The down-regulation of the sucAB genes that encode two subunits of KGDH was previously achieved by the replacement of the native promoter with the artificial $P_{tac}$-derived promoter, $P_{tac21}$ (U.S. Pat. No. 7,604,979 B2). It has been demonstrated in *E. coli* that the expression cassette cat-$P_{tac21}$-sucAB decreased KGDH activity by 60%, thereby elevating Glu accumulation 3-fold (U.S. Pat. No. 7,604,979 B2). This cassette was also introduced into the γ-EVG-producing strain MG1655 $P_L$-ilvG*MEDA ΔicdC::$P_{tac4071φ10}$-gshA50 attB φ80::$P_{tac4071φ10}$-gshB$^{M165F}$ $P_{L-SD1}$-kbl-tdh ΔgcvP::KmR (L1034-1) by P1 transduction. However, no positive effect on γ-EVG or γ-EV accumulation was observed in fed-batch EVG-cultivation. However, when using a flask for cultivation, the positive effect of sucAB genes down-regulation was observed (Table 4), namely, γ-EVG production increased about 2.5 times. Evidently, the difference in aeration conditions in flasks and jars was a key reason for the difference in evaluation results.

TABLE 4

Effect of sucAB genes expression.

| Strain | OD$_{540}$ | γ-EVG, g/L | γ-EV, g/L |
|---|---|---|---|
| L1034-1 | 11.3 ± 0.1 | 0.065 ± 0.005 | 0.07 ± 0.01 |
| L1034-1 cat-$P_{tac21}$-sucAB | 11.1 ± 0.5 | 0.16 ± 0.01 | 0.07 ± 0.01 |

Conditions: cultivation in flasks in the medium containing 4% of glucose and 10 g/L of Gly at 30° C. for 48 h; average data of 3 experiments are represented; HPLC data (Reference example 7).

Experimental procedure: cells from stock tube (stored in 25% glycerol, 0.9% NaCl at −70° C.) were placed on L-agar (yeast extract (Dia-M) 5 g/L, peptone (Dia-M) 10 g/L NaCl 5 g/L, agar 15 g/L). Cells from about one half of the plate surface were inoculated into 40 mL MS(+pyr) medium (Table 5) and cultivated for 24 hour at 30° C. at rotary shaker. After that, additional glucose was added to a final concentration of 20 g/L. After this addition, strains were cultivated for 24 hours at 30° C. on a rotary shaker. The total cultivation time was 48 h.

TABLE 5

The composition of the flask fermentation medium (MS + pyr medium) (g/L)

| | |
|---|---|
| Glucose | 20.0 |
| MgSO$_4$•7H$_2$O | 1.0 |
| (NH$_4$)$_2$SO$_4$ | 24.0 |
| KH$_2$PO$_4$•3H$_2$O | 1.0 |
| Yeast extract | 2.0 |
| FeSO$_4$•7H$_2$O | 10.0 |
| MnSO$_4$•5H$_2$O | 10.0 |
| Pyruvate | 0.5 |
| CaCO$_3$ | 30.0 |

Example 6

Positive Influence of tolC Overexpression on γ-EVG Production

To improve γ-EVG export, the expression of the tolC gene, that encodes an outer membrane protein involved in a range of tripartite efflux complexes (Benz R. et al., 1993), was increased. To this end, the expression cassette cat-$P_{Ltac}$-tolC (Reference example 5) was introduced into the γ-EVG-producing strain MG1655 $P_{L-SD1}$-ilvG*MEDA ΔicdC::$P_{tac4071φ10}$-gshA50 attB φ80::$P_{tac4071φ10}$-gshB$^{M165F}$ $P_{L-SD1}$-kbl-tdh ΔgcvP::KmR (L1034-1) by P1-transduction. Evaluation of the obtained strain L1034-1 cat-$P_{Ltac}$-tolC (L1036-1) in comparison with the parental strain demonstrated a positive effect of tolC gene overexpression on γ-EVG production, namely more than a 25% increase in γ-EVG accumulation when tolC is overexpressed (Table 6).

TABLE 6

| | Effect of tolC overexpression. | |
|---|---|---|
| Strain | MG1655 $P_L$-ilvG*MEDA $\Delta$icdC::$P_{tac4071\varphi10}$-gshA50 attB $\varphi$80::$P_{tac4071\varphi10}$-gshB$^{M165F}$ $P_{L-SD1}$-kbl-tdh $\Delta$gcvP::KmR (L1034-1) | L1034-1 cat-$P_{Ltac}$-tolC (L1036-1) |
| Biomass, g/B | 9.8 | 10.7 |
| Glucose, g/B | 37 | 39 |
| γ-EVG   g/L | 3.2 | 4.1 |
|          g/B | 1.1 | 1.5 |
| Yield, % | 3.0 | 3.8 |
| γ-EV, g/L | 2.2 | 2.8 |
| γ-EV/γ-EVG, % | 69 | 70 |

Conditions: fed-batch EVG-cultivation, mixed-feed, 24 h, HPLC data (Reference examples 6 and 7).

Reference Example 1

Construction of the Cassette attB phi80::KmR-Ptac4071φ10-gshB$^{M165F}$

A DNA fragment containing the gshB$^{M165F}$ gene was re-cloned from the plasmid pUC19-EcGshB*M165F (Reference example 4) into the integrative vector pAH162-λattL-TcR-λattR (Minaeva N. I., et al. Dual-In/Out strategy for genes integration into bacterial chromosome: a novel approach to step-by-step construction of plasmid-less marker-less recombinant E. coli strains with predesigned genome structure. BMC Biotechnology, 2008, 8:63) using the PstI/SacI restriction sites, yielding the delivery plasmid pAH162-GshB*M165F. The gene gshB$^{M165F}$ was inserted into the native φ80 locus by φ80 integrase-mediated recombination (Minaeva N. I., et al., 2008). Then, to achieve a high expression level, the regulatory region $P_{tac4071\varphi10}$ was introduced upstream of the gshB$^{M165F}$ gene by the Red-dependent integration method described above. According to this procedure, the PCR primers P17 (SEQ ID NO: 30) and P18 (SEQ ID NO: 31) were constructed. Oligonucleotide P17 (SEQ ID NO: 30) is homologous to the region upstream of the gshB$^{M165F}$ gene and the region adjacent to the KmR gene in the chromosomal DNA of the MG1655 $P_L$-SD1-kbl-tdh   $\Delta$gcvP   $P_L$-SD1-ilvG*MEDA   $\Delta$icdC::KmR-Ptac4071φ10-gshA50 strain, which was used as a template for PCR. Oligonucleotide P18 (SEQ ID NO: 31) is homologous to both the gshB$^{M165F}$ region and the region downstream to the $P^{tac4071\varphi10}$ regulatory region in the chromosome of the MG1655 $P_L$-SD1-kbl-tdh $\Delta$gcvP $P_L$-SD1-ilvG*MEDA $\Delta$icdC::KmR-P$_{tac4071}$φ10-gshA50 strain. Conditions for PCR were as follows: denaturation for 3 min at 95° C.; profile for two first cycles: 1 min at 95° C., 30 sec at 34° C., 80 sec at 72° C.; profile for the last 30 cycles: 30 sec at 95° C., 30 sec at 50° C., 80 sec at 72° C.; final step: 5 min at 72° C. The resulting 1721 bp DNA fragment (SEQ ID NO: 32) was purified by "Silica Bead DNA Gel Extraction Kit" ("Thermo Scientific") and used for electroporation of the strain MG1655 attB phi80::gshB$^{M165F}$ containing the plasmid pKD46. Kanamycin-resistant recombinants were selected; the introduction of Ptac4071φ10 promoter marked with the KmR resistance gene was confirmed by PCR using locus-specific primers P7 (SEQ ID NO: 33) and P8 (SEQ ID NO: 34). Conditions for PCR verification were as follows: denaturation for 5 min at 94° C.; profile for the 25 cycles: 30 sec at 94° C., 30 sec at 59° C., 1 min at 72° C.; final step: 7 min at 72° C. The DNA fragment obtained in the reaction with the MG1655 strain used as a template was 274 nt in length (SEQ ID NO: 35). The DNA fragment obtained in the reaction with the MG1655 attB phi80::KmR-Ptac4071φ10-gshB*M165F strain as a template was 1917 nt in length (SEQ ID NO: 36). As a result, the strain MG1655 attB phi80::KmR-Ptac4071φ10-gshB$^{M165F}$ was obtained.

Reference Example 2

Construction of the Cassette $P_{L-SD1}$-ilvG*M-$\Delta$ilvE:: cat-DA

The cassette $P_{L-SD1}$-ilvG*M-$\Delta$ilvE::cat-DA was constructed by the method of Red-dependent integration described above. According to this procedure, the PCR primers P19 (SEQ ID NO: 37) and P20 (SEQ ID NO: 38) were constructed. These primers are homologous to both the region adjacent to the ilvE gene and the gene that confers chloramphenicol resistance in the template plasmid pMW-attL-Cm-attR (PCT application WO 05/010175). Conditions for PCR were as follows: denaturation step for 3 min at 95° C.; profile for two first cycles: 1 min at 95° C., 30 sec at 34° C., 80 sec at 72° C.; profile for the last 28 cycles: 30 sec at 95° C., 30 sec at 50° C., 80 sec at 72° C.; final step: 7 min at 72° C. The obtained DNA fragment (1713 bp) (SEQ ID NO: 39) was purified by "Silica Bead DNA Gel Extraction Kit" ("Thermo Scientific") and used for electroporation of the strain MG1655 $P_{L-SD1}$-ilvG*MEDA containing the plasmid pKD46. Chloramphenicol resistant recombinants were selected and the deletion of ilvE gene marked with Cm$^R$ gene in selected mutants was verified by PCR using locus-specific primers P21 (SEQ ID NO: 40) and P22 (SEQ ID NO: 41). Conditions for PCR verification were following: denaturation step for 5 min at 94° C.; profile for the 25 cycles: 30 sec at 94° C., 30 sec at 57° C., 1 min at 72° C.; final step: 7 min at 72° C. The DNA fragment obtained in the reaction with the parental strain MG1655 $P_{L-SD1}$-ilvG*MEDA as a template was 1354 nt in length (SEQ ID NO: 42). Thee DNA fragment obtained in the reaction with the MG1655 $P_{L-SD1}$-ilvG*M-$\Delta$ilvE::cat-DA strain as a template, was 2015 nt in length (SEQ ID NO: 43)

Reference Example 3

Construction of the Expression Cassette $\Delta$icdC:: KmR-P$_{tac4071\varphi10}$-gshA50

Using pSF12-gshA*50 (described in US 2016326510 A1) as a template, PCR was carried out with primer pair P23 (SEQ ID NO: 44) and P24 (SEQ ID NO: 45) to add scaffold nucleotides at the edge of the gshA*50 fragment for fusion-PCR with a chemically synthesized Ptac4071f10 fragment (SEQ ID NO: 46). Then, the gshA*50 fragment with scaffold and Ptac4071f10 fragment were mixed and used as the template in fusion-PCR using primer pair P24 (SEQ IIS NO: 45) and P25 (SEQ ID NO: 47) to construct Ptac4071f10-gshA*50 fragment. The Ptac4071f10-gshA*50 fragment was cloned into XbaI restriction site of pMW118-attL-kan-attR plasmid (Japanese Patent Laid-open No. 2005-058227, WO2005/010175) using in-fusion technique (In-Fusion HD cloning Kit, Clontech). The constructed plasmid was designated as pMW118-attL-kan-attR-Ptac4071f10-gshA*50. KmR-Ptac4071f10-gshA50 cassette was amplified by PCR using primer pair P26 (SEQ ID NO: 48) and P27 (SEQ ID NO: 49), and pMW118-attL-kan-attR-Ptac4071f10-gshA*50 as a template. The obtained DNA fragment was introduced into strain E. coli K-12 MG1655 strain (ATCC 47076) using λ-red technique (Datsenko K. A. and Wanner B. L., *Proc. Natl. Acad. Sci. USA* 2000, 97(12):6640-45; Zhang Y. et al., *Nature Genet.*, 1998, 20:123-128). This constructed strain was designated as MG1655ΔicdC::attL-kan-attR-Ptac4071f10-gshA*50 harboring the cassette ΔicdC:KmR-P$_{tac4071\varphi10}$-gshA50.

Reference Example 4

Construction of the Cassette attB φ80::CatR-P$_{tac4071\varphi10}$-gshB$^{M165F}$ At first, gshB expression plasmid pUC19-Plac-gshB was prepared. A gshB fragment was amplified using primer pair P28 (SEQ ID NO: 50) and P29 (SEQ ID NO: 51), and chromosomal DNA of MG1655 strain as a template. The gshB fragment was cloned at XbaI site of pUC19 (New England Biolabs) using in-fusion technique (In-Fusion HD cloning Kit, Clontech). Then, pUC19-Plac-gshB*M165F was prepared b carrying out PCR using primer pairs P30 (SEQ ID NO: 52) and P31 (SEQ ID NO: 53), and pUC19-Plac-gshB as a template. After digesting the obtained PCR fragment with DpnI to degrade the PCR template pUC19-Plac-ghB, competent cells JM109 (available from Takara Bio) were transformed with the PCR solution to obtain gshB*M165F expression plasmid pUC19-Plac-gshB*M165F.

Using pUC19-Plac-gshB*M165F as a template, a PCR was carried out using primer pairs P32 (SEQ ID NO: 54) and P33 (SEQ ID NO: 55) to add scaffold nucleotides at the edge of gshB*M165F fragment for fusion-PCR with chemically synthesized Ptac4071f10 fragment (SEQ ID NO: 46). Then, gshB*M165F fragment with scaffold and Ptac4071f10 fragment were mixed and used as template in fusion-PCR using primer pairs P25 (SEQ ID NO: 47) and P33 (SEQ ID NO: 55) to construct Ptac4071f10-gshB*M165F fragment. The Ptac4070f10-gshB*M165F fragment was cloned into XbaI site of pMW118-attL-cat-attR plasmid by in-fusion technique (In-Fusion HD cloning Kit, Clontech). This constructed plasmid was designated as pMW118-attL-cat-attR-Ptac4071f10-gshB*M165F. CatR-Ptac4071f10-gshB*M165F cassette was amplified by PCR using primer pair P34 (SEQ ID NO: 56) and P35 (SEQ ID NO: 57), and pMW118-attL-cat-attR-Ptac4071f10-gshB*M165F as a template. The obtained DNA fragment was introduced into strain MG1655ΔicdC::attL-kan-attR-Ptac4071f10-gshA*50 (Reference example 3) by λ-red technique. Constructed strain was designated as MG1655ΔicdC::attL-kan-attR-Ptac4071f10-gshA*50 ΔgshB::attL-cat-attR-Ptac4071f10-gshB*M165F harboring the cassette attB φ80::CatR-P$_{tac4071\varphi10}$-gshB$^{M165F}$.

Reference Example 5

Construction of the Expression Cassette cat-P$_{Ltac}$-tolC

The tolC gene was overexpressed using the method of Red-dependent integration (Datsenko K. A. and Wanner B. L., Proc. Natl. Acad. Sci. USA, 2000, 97(12):6640-45). According to this procedure, the PCR primers P36 (SEQ ID NO: 61) and P37 (SEQ ID NO: 62), which are homologous to both regions adjacent to the tolC gene and regions adjacent to the chloramphenicol resistance gene (CmR) and the P$_{Ltac}$ promoter in the template chromosome, were constructed. The chromosome of the strain MG1655 cat-P$_{L-tac}$-xylE, which contains hybrid P$_{Ltac}$ promoter, was used as the template in PCR reaction. The strain MG1655 cat-P$_{Ltac}$- xylE can be constructed as described in detail in WO2006/043730. Conditions for PCR were as follows: denaturation for 3 min at 95° C.; profile for two first cycles: 1 min at 95° C., 30 sec at 34° C., 80 sec at 72° C.; profile for the last 30 cycles: 30 sec at 95° C., 30 sec at 50° C., 80 sec at 72° C.; final step: 5 min at 72° C. The obtained DNA fragment (1791 bp) (SEQ ID NO: 58) was purified by "Silica Bead DNA Gel Extraction Kit" ("Thermo Scientific"), and used for electroporation of the *E. coli* strain MG1655 containing the plasmid pKD46. Chloramphenicol resistant recombinants were selected after electroporation. The replacement of the native regulatory region of tolC gene with the P$_{Ltac}$ promoter region, marked with the Cm resistance gene, was confirmed by PCR using locus-specific primers P38 (SEQ ID NO: 63) and P39 (SEQ ID NO: 64). Conditions for PCR verification were the following: denaturation for 3 min at 5° C.; profile for the 30 cycles: 30 sec at 95° C., 30 sec at 57° C., 1 min at 72° C.; final step: 7 min at 72° C. DNA fragment (SEQ ID NO: 59), obtained in the reaction with the cells of MG1655 strain used as a template, was 500 nt in length. DNA fragment (SEQ ID NO: 60), obtained in the reaction with the cells of MG1655 cat-P$_{Ltac}$-tolC strain as a template, was 2279 nt in length. Then, the plasmid pKD46 was eliminated by cultivation at 42° C. Thus, the *E. coli* strain MG1655 harboring the expression cassette cat-P$_{Ltac}$-tolC was constructed.

Reference Example 6

EVG-Cultivation

For each of the above examples, the following culture conditions were used for EVG-cultivation.

All *E. coil* strains were maintained on LB agar plates at 4° C. LB agar (2%) was used for pre-cultivation of all investigated strains at 37° C. overnight during 17 h.

Seed culture was conducted in GALLENCAMP shaker in 750-mL Erlenmeyer flask on LB liquid media (volume of the media was 50 mL) during 5 h. Temperature of cultivation was 37° C., rotation speed was 240 rpm. One loop of biomass from pre-cultivated plate was used for inoculation of seed culture.

Main culture was conducted in 1 L S-Jars (ABLE Biott). Cultivating conditions were as follows: agitation at 1200 rpm was fixed, aeration 1/1 vvm, temperature 37° C., pH 6.6 was maintained using NH$_3$ gas. Dissolved Oxygen level was controlled as follows: if DO level become 0% (DO limiting condition occurred) DO level was maintained at 2% after DO limitation stopped by dropping down agitation. If DO level did not reach 0% no DO control was used. Media volume was 300 mL, inoculation volume of seed culture was 10%.

The composition of the medium used for main culture is shown in Table 7.

TABLE 7

| Glucose | 30.0 | g/L |
|---|---|---|
| MgSO$_4$•7H$_2$O | 2.4 | g/L |
| Mamero (Hydrolyzed soy bean solution, TN = 35 g/L) | 0.4 | g/L |
| KH$_2$PO$_4$ | 6.0 | g/L |
| (NH$_4$)$_2$SO$_4$ | 5.0 | g/L |
| FeSO$_4$•7H$_2$O | 20.0 | mg/L |
| MnSO$_4$•5H$_2$O | 20.0 | mg/L |
| Vitamin B1 (Thiamine hydrochloride) | 0.4 | mg/L |

TABLE 7-continued

| | | |
|---|---|---|
| Antifoam GD-113 (manufactured by NOF Corporation) | 0.02 | mL/L |

After 6 h of cultivation, glucose feeding solution (concentration 700 g/L) was continuously added to maintain glucose level in the culture broth within the range of 10-25 g/L. Culture time of main process in total was 24 h.

Reference Example 7

HPLC Analysis

Similarly, for each of the above examples, the HPLC analysis was conducted as follows.

Analysis of γ-EVG was done using high performance liquid chromatography (HPLC). A modified AccQ*Tag method was used for the analysis of samples, with pre-column derivatization.

Equipment: Agilent 1100, with fluorescence detector.

Column: Waters AccQ*Tag 3.9×150 mm (Part No. WAT052885).

Reagent for derivatization: AccQ-Fluor Reagent Kit (WAT052880).

Conditions for the derivatization: 25 μL of buffer from the AccQ-Fluor Reagent Kit, 5 μL of sample, 20 μL of reagent from the AccQ-Fluor Reagent Kit. Mix and incubate at 55° C. for 10 min.

Eluent:

A: 10% aqueous solution of AccQ*Tag Eluent A (WAT052890)

B: 80% aqueous solution of acetonitrile (HPLC grade)

Time of injection: 38 min.

Volume of injection: 5 μL.

Detection: $\lambda_{ex}$—250 nm, $\lambda_{em}$—395 nm.

Column temperature: 30° C.

Flow rate: 0.8 mL/min.

Gradient: Table 8

TABLE 8

| Time | A % | B % |
|---|---|---|
| 0.00 | 100.0 | 0.0 |
| 0.50 | 100.0 | 0.0 |
| 2.00 | 96.8 | 3.2 |
| 15.00 | 95.8 | 4.2 |
| 19.00 | 93.5 | 6.5 |
| 20.00 | 89.5 | 10.5 |
| 24.00 | 82.0 | 18.0 |
| 30.00 | 81.2 | 18.8 |
| 30.10 | 80.0 | 20.0 |
| 32.10 | 80.0 | 20.0 |
| 32.20 | 0.0 | 100.0 |
| 38.00 | 0.0 | 100.0 |

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

INDUSTRIAL APPLICABILITY

The method of the present invention is useful for the production of a tripeptide γ-Glu-Val-Gly by fermentation of a bacterium.

The invention claimed is:

1. A method for producing γ-Glu-Val-Gly, the method comprising:

(i) cultivating a γ-Glu-Val-Gly-producing bacterium belonging to the family Enterobacteriaceae in a culture medium so that the γ-Glu-Val-Gly is produced and accumulates in the culture medium or the cells of the bacterium, or both, and (ii) collecting the γ-Glu-Val-Gly from the culture medium or the cells of the bacterium, or both, wherein the bacterium has been modified to overexpress a gene encoding a protein having L-threonine 3-dehydrogenase activity and a gene encoding a protein having 2-amino-3-oxobutanoate coenzyme A ligase activity, wherein the bacterium has been modified to overexpress a tolC gene, wherein the tolC gene is overexpressed by transformation with a DNA comprising the tolC gene, a mutation of a promoter of the tolC gene, a mutation of a Shine-Dalgarno (SD) sequence of the tolC gene, a mutation of a spacer between the SD sequence and start codon of the tolC gene, a mutation of a ribosome-binding site of the tolC gene, and combinations thereof, and wherein the cultivating step (i) is carried out at a pH from 6.6 to 7.5.

2. The method according to claim 1, wherein the gene encoding a protein having L-threonine 3-dehydrogenase activity is a tdh gene, and the gene encoding a protein having 2-amino-3-oxobutanoate coenzyme A ligase activity is a kbl gene.

3. The method according to claim 1, wherein the protein having L-threonine 3-dehydrogenase activity is selected from the group consisting of:

(A) a protein comprising the amino acid sequence of SEQ ID NO: 2, (B) a protein comprising the amino acid sequence of SEQ ID NO: 2 having a substitution, deletion, insertion and/or addition of 1 to 50 amino acid residues, and wherein the protein has L-threonine 3-dehydrogenase activity, and (C) a protein comprising an amino acid sequence having an identity of not less than 60% with respect to the entire amino acid sequence of SEQ ID NO: 2, and wherein the protein has L-threonine 3-dehydrogenase activity;

and wherein the protein having 2-amino-3-oxobutanoate coenzyme A ligase activity is selected from the group consisting of:

(D) a protein comprising the amino acid sequence of SEQ ID NO: 4, (E) a protein comprising the amino acid sequence of SEQ ID NO: 4 having a substitution, deletion, insertion and/or addition of 1 to 50 amino acid residues, and wherein the protein has 2-amino-3-oxobutanoate coenzyme A ligase activity, and (F) a protein comprising an amino acid sequence having an identity of not less than 60% with respect to the entire amino acid sequence of SEQ ID NO: 4, and wherein the protein has 2-amino-3-oxobutanoate coenzyme A ligase activity.

4. The method according to claim 1, wherein the protein having L-threonine 3-dehydrogenase activity is encoded by a DNA selected from the group consisting of:

(a) a DNA comprising the nucleotide sequence of SEQ ID NO: 1, (b) a DNA comprising a nucleotide sequence that is able to hybridize under a stringent condition with a nucleotide sequence complementary to the sequence of SEQ ID NO: 1, wherein the stringent condition comprises washing three times, at a salt concentration of 0.1×SSC, 0.1% SDS at 65° C., (c) a DNA encoding a protein comprising the amino acid sequence of SEQ ID NO: 2 having a substitution, deletion, insertion and/or addition of 1 to 50 amino acid residues, and wherein the protein has L-threonine 3-dehydrogenase activity, and (d) a DNA which is a variant nucleotide sequence of SEQ ID NO: 1 due to the degeneracy of the genetic code;

and wherein the protein having 2-amino-3-oxobutanoate coenzyme A ligase is encoded by a DNA selected from the group consisting of:

(e) a DNA comprising the nucleotide sequence of SEQ ID NO: 3, (f) a DNA comprising a nucleotide sequence that is able to hybridize under a stringent condition with a nucleotide sequence complementary to the sequence of SEQ ID NO: 3, wherein the stringent condition comprises washing three times, at a salt concentration of 0.1×SSC, 0.1% SDS at 65° C., (g) a DNA encoding a protein comprising the amino acid sequence of SEQ ID NO: 4 having a substitution, deletion, insertion and/or addition of 1 to 50 amino acid residues, and wherein the protein has 2-amino-3-oxobutanoate coenzyme A ligase activity, and (h) a DNA which is a variant nucleotide sequence of SEQ ID NO: 3 due to the degeneracy of the genetic code.

5. The method according to claim 1, wherein the gene encoding the protein having L-threonine 3-dehydrogenase activity and the gene encoding the protein having 2-amino-3-oxobutanoate coenzyme A ligase activity are each over-expressed by a method selected from the group consisting of:

(i) increasing the copy number of the gene or genes in the bacterium, (ii) modifying an expression regulatory region of the gene or genes in the bacterium, and (iii) combinations thereof, wherein the expression of the genes is increased as compared with a bacterium that has not been modified to overexpress a gene encoding a protein having L-threonine 3-dehydrogenase activity and a gene encoding a protein having 2-amino-3-oxobutanoate coenzyme A ligase activity.

6. The method according to claim 1, wherein the bacterium has been modified further by a method selected from the group consisting of:

(i) attenuating expression of a gcvP gene as compared with a bacterium that has not been modified to attenuate expression of a gcvP gene, (ii) attenuating expression of sucAB operon genes as compared with a bacterium that has not been modified to attenuate expression of sucAB operon genes, (iii) overexpressing ilVGMEDA operon genes, or (iv) a combination thereof.

7. The method according to claim 6, wherein the ilVGMEDA operon genes comprise an ilvG gene that encodes an enzymatically active acetolactate synthase II.

8. The method according to claim 1, wherein the bacterium belongs to the genus *Escherichia* or *Pantoea.*

9. The method according to claim 8, wherein the bacterium is *Escherichia coli* or *Pantoea ananatis.*

10. The method according to claim 1, wherein the pH of the cultivating step (i) is 6.6.

* * * * *

SEQUENCE LISTING

<160> NUMBER OF SEQ ID NOS: 64

<210> SEQ ID NO 1
<211> LENGTH: 1026
<212> TYPE: DNA
<213> ORGANISM: Escherichia coli

<400> SEQUENCE: 1

```
atgaaagcgt tatccaaact gaaagcggaa gagggcatct ggatgaccga cgttcctgta        60
ccggaactcg ggcataacga tctgctgatt aaaatccgta aaacagccat ctgcgggact       120
gacgttcaca tctataactg ggatgagtgg tcgcaaaaaa ccatcccggt gccgatggtc       180
gtgggccatg aaatatgtcg gtgaagtggta ggtattggtc aggaagtgaa aggcttcaag       240
atcggcgatc gcgtttctgg cgaaggccat atcacctgtg gtcattgccg caactgtcgt       300
ggtggtcgta cccatttgtg ccgcaacacg ataggcgttg gtgttaatcg cccgggctgc       360
tttgccgaat atctggtgat cccggcattc aacgccttca aaatccccga caatatttcc       420
gatgacttag ccgcaatttt tgatcccttc ggtaacgccg tgcataccgc gctgtcgttt       480
gatctggtgg gcgaagatgt gctggtttct ggtgcaggcc cgattggtat tatggcagcg       540
gcggtggcga aacacgttgg tgcacgcaat gtggtgatca ctgatgttaa cgaataccgc       600
cttgagctgg cgcgtaaaat gggtatcacc cgtgcggtta acgtcgccaa agaaaatctc       660
aatgacgtga tggcggagtt aggcatgacc gaaggttttg atgtcggtct ggaaatgtcc       720
ggtgcgccgc cagcgtttcg taccatgctt gacaccatga tcacggcgg ccgtattgcg        780
```

-continued

```
atgctgggta ttccgccgtc tgatatgtct atcgactgga ccaaagtgat ctttaaaggc      840
ttgttcatta aaggtattta cggtcgtgag atgtttgaaa cctggtacaa gatggcggcg      900
ctgattcagt ctggcctcga tctttcgccg atcattaccc atcgtttctc tatcgatgat      960
ttccagaagg gctttgacgc tatgcgttcg ggccagtccg ggaaagttat tctgagctgg      1020
gattaa                                                                 1026
```

<210> SEQ ID NO 2
<211> LENGTH: 341
<212> TYPE: PRT
<213> ORGANISM: Escherichia coli

<400> SEQUENCE: 2

```
Met Lys Ala Leu Ser Lys Leu Lys Ala Glu Glu Gly Ile Trp Met Thr
1               5                   10                  15

Asp Val Pro Val Pro Glu Leu Gly His Asn Asp Leu Leu Ile Lys Ile
            20                  25                  30

Arg Lys Thr Ala Ile Cys Gly Thr Asp Val His Ile Tyr Asn Trp Asp
        35                  40                  45

Glu Trp Ser Gln Lys Thr Ile Pro Val Pro Met Val Val Gly His Glu
    50                  55                  60

Tyr Val Gly Glu Val Val Gly Ile Gly Gln Glu Val Lys Gly Phe Lys
65                  70                  75                  80

Ile Gly Asp Arg Val Ser Gly Glu Gly His Ile Thr Cys Gly His Cys
                85                  90                  95

Arg Asn Cys Arg Gly Gly Arg Thr His Leu Cys Arg Asn Thr Ile Gly
            100                 105                 110

Val Gly Val Asn Arg Pro Gly Cys Phe Ala Glu Tyr Leu Val Ile Pro
        115                 120                 125

Ala Phe Asn Ala Phe Lys Ile Pro Asp Asn Ile Ser Asp Asp Leu Ala
        130                 135                 140

Ala Ile Phe Asp Pro Phe Gly Asn Ala Val His Thr Ala Leu Ser Phe
145                 150                 155                 160

Asp Leu Val Gly Glu Asp Val Leu Val Ser Gly Ala Gly Pro Ile Gly
                165                 170                 175

Ile Met Ala Ala Ala Val Ala Lys His Val Gly Ala Arg Asn Val Val
            180                 185                 190

Ile Thr Asp Val Asn Glu Tyr Arg Leu Glu Leu Ala Arg Lys Met Gly
        195                 200                 205

Ile Thr Arg Ala Val Asn Val Ala Lys Glu Asn Leu Asn Asp Val Met
    210                 215                 220

Ala Glu Leu Gly Met Thr Glu Gly Phe Asp Val Gly Leu Glu Met Ser
225                 230                 235                 240

Gly Ala Pro Pro Ala Phe Arg Thr Met Leu Asp Thr Met Asn His Gly
                245                 250                 255

Gly Arg Ile Ala Met Leu Gly Ile Pro Pro Ser Asp Met Ser Ile Asp
            260                 265                 270

Trp Thr Lys Val Ile Phe Lys Gly Leu Phe Ile Lys Gly Ile Tyr Gly
        275                 280                 285

Arg Glu Met Phe Glu Thr Trp Tyr Lys Met Ala Ala Leu Ile Gln Ser
    290                 295                 300

Gly Leu Asp Leu Ser Pro Ile Ile Thr His Arg Phe Ser Ile Asp Asp
305                 310                 315                 320

Phe Gln Lys Gly Phe Asp Ala Met Arg Ser Gly Gln Ser Gly Lys Val
```

```
                    325                 330                 335

Ile Leu Ser Trp Asp
            340

<210> SEQ ID NO 3
<211> LENGTH: 1197
<212> TYPE: DNA
<213> ORGANISM: Escherichia coli

<400> SEQUENCE: 3
atgcgtggag aattttatca gcagttaacc aacgatctgg aaaccgcacg ggcggaaggg      60
ttgtttaaag aagagcgcat tattacgtct gcgcagcaag cagatatcac tgtggctgat     120
ggaagccacg tcattaactt ttgtgccaac aactatctcg ggctggcgaa tcatcctgat     180
ctgattgcgg cggcaaaggc gggaatggat tctcacggtt tcggcatggc ttcggtgcgt     240
tttatttgcg gcactcagga cagccataaa gagcttgaac aaaaactggc ggccttcctg     300
gggatggaag atgcgattct ctactcttcc tgctttgatg ctaacggtgg cctgtttgaa     360
acgcttctgg gtgcggaaga cgccattatc tccgacgcac tgaaccacgc gtctattatt     420
gatggtgtgc gtctgtgcaa agctaaacgc tatcgctatg ccaacaacga tatgcaggag     480
ctggaagcac gtctgaaaga agcgcgtgaa gccggtgcgc gtcatgtgct gatcgccacc     540
gatggtgtgt ctcaatgga cggcgtgatt gccaacctga agggcgtttg cgatctggca     600
gataaatatg atgccctggt gatggtagac gactcccacg cggtcggttt tgtcggtgaa     660
aatggtcgtg gttcccatga atactgcgat gtgatgggcc gggtcgatat tatcaccggt     720
acgcttggta aagcgctggg cggggcttct ggtggttata ccgcggcgcg caaagaagtg     780
gttgagtggc tgcgccagcg ttctcgtccg tacctgttct ccaactcgct ggcaccggcc     840
attgttgccg cgtccatcaa agtactggag atggtcgaag cgggcagcga actgcgtgac     900
cgtctgtggg cgaacgcgcg tcagttccgt gagcaaatgt cggcggcggg ctttaccctg     960
gcgggagccg atcacgccat tattccggtc atgcttggtg atgcggtagt ggcgcagaaa    1020
tttgcccgtg agctgcaaaa agagggcatt tacgttaccg gtttcttcta tccggtcgtt    1080
ccgaaaggtc aggcgcgtat tcgtacccag atgtctgcgg cgcataccce tgagcaaatt    1140 acgcgtgcag tagaagcatt tacgcgtatt ggtaaacaac tgggcgttat cgcctga      1197

<210> SEQ ID NO 4
<211> LENGTH: 398
<212> TYPE: PRT
<213> ORGANISM: Escherichia coli

<400> SEQUENCE: 4

Met Arg Gly Glu Phe Tyr Gln Gln Leu Thr Asn Asp Leu Glu Thr Ala
1               5                   10                  15

Arg Ala Glu Gly Leu Phe Lys Glu Glu Arg Ile Ile Thr Ser Ala Gln
            20                  25                  30

Gln Ala Asp Ile Thr Val Ala Asp Gly Ser His Val Ile Asn Phe Cys
        35                  40                  45

Ala Asn Asn Tyr Leu Gly Leu Ala Asn His Pro Asp Leu Ile Ala Ala
    50                  55                  60

Ala Lys Ala Gly Met Asp Ser His Gly Phe Gly Met Ala Ser Val Arg
65                  70                  75                  80

Phe Ile Cys Gly Thr Gln Asp Ser His Lys Glu Leu Glu Gln Lys Leu
                85                  90                  95
```

-continued

```
Ala Ala Phe Leu Gly Met Glu Asp Ala Ile Leu Tyr Ser Ser Cys Phe
            100                 105                 110

Asp Ala Asn Gly Gly Leu Phe Glu Thr Leu Leu Gly Ala Glu Asp Ala
        115                 120                 125

Ile Ile Ser Asp Ala Leu Asn His Ala Ser Ile Ile Asp Gly Val Arg
    130                 135                 140

Leu Cys Lys Ala Lys Arg Tyr Arg Tyr Ala Asn Asn Asp Met Gln Glu
145                 150                 155                 160

Leu Glu Ala Arg Leu Lys Glu Ala Arg Glu Ala Gly Ala Arg His Val
                165                 170                 175

Leu Ile Ala Thr Asp Gly Val Phe Ser Met Asp Gly Val Ile Ala Asn
            180                 185                 190

Leu Lys Gly Val Cys Asp Leu Ala Asp Lys Tyr Asp Ala Leu Val Met
        195                 200                 205

Val Asp Asp Ser His Ala Val Gly Phe Val Gly Glu Asn Gly Arg Gly
    210                 215                 220

Ser His Glu Tyr Cys Asp Val Met Gly Arg Val Asp Ile Ile Thr Gly
225                 230                 235                 240

Thr Leu Gly Lys Ala Leu Gly Gly Ala Ser Gly Gly Tyr Thr Ala Ala
                245                 250                 255

Arg Lys Glu Val Val Glu Trp Leu Arg Gln Arg Ser Arg Pro Tyr Leu
                260                 265                 270

Phe Ser Asn Ser Leu Ala Pro Ala Ile Val Ala Ala Ser Ile Lys Val
            275                 280                 285

Leu Glu Met Val Glu Ala Gly Ser Glu Leu Arg Asp Arg Leu Trp Ala
        290                 295                 300

Asn Ala Arg Gln Phe Arg Glu Gln Met Ser Ala Ala Gly Phe Thr Leu
305                 310                 315                 320

Ala Gly Ala Asp His Ala Ile Ile Pro Val Met Leu Gly Asp Ala Val
                325                 330                 335

Val Ala Gln Lys Phe Ala Arg Glu Leu Gln Lys Glu Gly Ile Tyr Val
                340                 345                 350

Thr Gly Phe Phe Tyr Pro Val Val Pro Lys Gly Gln Ala Arg Ile Arg
            355                 360                 365

Thr Gln Met Ser Ala Ala His Thr Pro Glu Gln Ile Thr Arg Ala Val
        370                 375                 380

Glu Ala Phe Thr Arg Ile Gly Lys Gln Leu Gly Val Ile Ala
385                 390                 395
```

```
<210> SEQ ID NO 5
<211> LENGTH: 64
<212> TYPE: DNA
<213> ORGANISM: Artificial Sequence
<220> FEATURE:
<223> OTHER INFORMATION: Primer P1

<400> SEQUENCE: 5
aaaggatgaa ctacgaggaa gggaacaaca ttcatacgct caagttagta taaaaaagct        60
gaac                                                                     64

<210> SEQ ID NO 6
<211> LENGTH: 70
<212> TYPE: DNA
<213> ORGANISM: Artificial Sequence
<220> FEATURE:
<223> OTHER INFORMATION: Primer P2
```

-continued

```
<400> SEQUENCE: 6
atgtaccacc cactgtgcgc cattcatagt tagttctcct tccggccaat gcttcgtttc      60
gtatcacaca                                                            70

<210> SEQ ID NO 7
<211> LENGTH: 1957
<212> TYPE: DNA
<213> ORGANISM: Artificial Sequence
<220> FEATURE:
<223> OTHER INFORMATION: DNA fragment

<400> SEQUENCE: 7
aaaggatgaa ctacgaggaa gggaacaaca ttcatacgct caagttagta taaaaaagct      60
gaacgagaaa cgtaaaatga tataaatatc aatatattaa attagatttt gcataaaaaa     120
cagactacat aatactgtaa aacacaacat atgcagtcac tatgaatcaa ctacttagat     180
ggtattagtg acctgtaaca gactgcagtg gtcgaaaaaa aaagcccgca ctgtcaggtg     240
cgggcttttt tctgtgttaa gcttcgacga atttctgcca ttcatccgct tattatcact     300
tattcaggcg tagcaccagg cgtttaaggg caccaataac tgccttaaaa aaattacgcc     360
ccgccctgcc actcatcgca gtactgttgt aattcattaa gcattctgcc gacatggaag     420
ccatcacaga cggcatgatg aacctgaatc gccagcggca tcagcacctt gtcgccttgc     480
gtataatatt tgcccatggt gaaaacgggg gcgaagaagt tgtccatatt ggccacgttt     540
aaatcaaaac tggtgaaact cacccaggga ttggctgaga cgaaaaacat attctcaata     600
aaccctttag ggaaataggc caggttttca ccgtaacacg ccacatcttg cgaatatatg     660
tgtagaaact gccggaaatc gtcgtggtat tcactccaga gcgatgaaaa cgtttcagtt     720
tgctcatgga aaacggtgta acaagggtga acactatccc atatcaccag ctcaccgtct     780
ttcattgcca tacggaattc cggatgagca ttcatcaggc gggcaagaat gtgaataaag     840
gccggataaa acttgtgctt attttttcttt acggtcttta aaaaggccgt aatatccagc     900
tgaacggtct ggttataggt acattgagca actgactgaa atgcctcaaa atgttcttta     960
cgatgccatt gggatatatc aacggtggta tatccagtga ttttttttctc catttttagct    1020 tccttagctc ctgaaaatct cggatccgat atctagctag agcgcccggt tgacgctgct    1080
agtgttacct agcgatttgt atcttactgc atgttacttc atgttgtcaa tacctgtttt    1140
tcgtgcgact tatcaggctg tctacttatc cggagatcca caggacgggt gtggtcgcca    1200
tgatcgcgta gtcgatagtg gctccaagta gcgaagcgag caggactggg cggcggccaa    1260
agcggtcgga cagtgctccg agaacgggtg cgcatagaaa ttgcatcaac gcatatagcg    1320
ctagcagcac gccatagtga ctggcgatgc tgtcggaatg gacgatatcc cgcaagaggc    1380
ccggcagtac cggcataacc aagcctatgc ctacagcatc cagggtgacg gtgccgagga    1440
tgacgatgag cgcattgtta gatttcatac acggtgcctg actgcgttag caatttaact    1500
gtgataaact accgcattaa agcttatcga tgataagctg tcaaacatga gaattcgaaa    1560
tcaaataatg attttatttt gactgatagt gacctgttcg ttgcaacaaa ttgataagca    1620
atgctttttt ataatgccaa cttagtataa aaaagcaggc ttcaagatct tcacctacca    1680
aacaatgccc ccctgcaaaa aataaattca tataaaaaac atacagataa ccatctgcgg    1740
tgataaatta tctctggcgg tgttgacata aataccactg gcggtgatac tgagcacatc    1800
agcaggacgc actgaccacc atgaaggtga cgctcttaaa aattaagccc tgaagaaggg    1860
cagcattcaa agcagaaggc tttggggtgt gtgatacgaa acgaagcatt ggccggaagg    1920
```
agaactaact atgaatggcg cacagtgggt ggtacat                              1957

<210> SEQ ID NO 8
<211> LENGTH: 22
<212> TYPE: DNA
<213> ORGANISM: Artificial Sequence
<220> FEATURE:
<223> OTHER INFORMATION: Primer P3

<400> SEQUENCE: 8
tgcaagtgaa gttgagttgt tc                                              22

<210> SEQ ID NO 9
<211> LENGTH: 21
<212> TYPE: DNA
<213> ORGANISM: Artificial Sequence
<220> FEATURE:
<223> OTHER INFORMATION: Primer P4

<400> SEQUENCE: 9
gataaccgaa aacggtgttc a                                               21

<210> SEQ ID NO 10
<211> LENGTH: 566
<212> TYPE: DNA
<213> ORGANISM: Artificial Sequence
<220> FEATURE:
<223> OTHER INFORMATION: DNA fragment

<400> SEQUENCE: 10
tgcaagtgaa gttgagttgt tctggcggtg gaatgatgct cgcaaaaatg cagcggacaa    60
aggatgaact acgaggaagg gaacaacatt catactgaaa ttgaattttt ttcactcact   120
attttatttt taaaaaacaa caatttatat tgaaattatt aaacgcatca taaaaatcgg   180
ccaaaaaata tcttgtacta tttacaaaac ctatggtaac tctttaggca ttccttcgaa   240
caagatgcaa gaaaagacaa aatgacagcc cttctacgag tgattagcct ggtcgtgatt   300
agcgtggtgg tgattattat cccaccgtgc ggggctgcac ttggacgagg aaaggcttag   360
agatcaagcc ttaacgaact aagaccccg caccgaaagg tccggggggtt tttttttgacc  420 ttaaaaacat aaccgaggag cagacaatga ataacagcac aaaattctgt ttctcaagat   480
tcaggacggg gaactaacta tgaatggcgc acagtgggtg gtacatgcgt tgcgggcaca   540
gggtgtgaac accgttttcg gttatc                                        566

<210> SEQ ID NO 11
<211> LENGTH: 2055
<212> TYPE: DNA
<213> ORGANISM: Artificial Sequence
<220> FEATURE:
<223> OTHER INFORMATION: DNA fragment

<400> SEQUENCE: 11
tgcaagtgaa gttgagttgt tctggcggtg gaatgatgct cgcaaaaatg cagcggacaa    60
aggatgaact acgaggaagg gaacaacatt catacgctca agttagtata aaaaagctga   120
acgagaaacg taaaatgata taaatatcaa tatattaaat tagattttgc ataaaaaaca   180
gactacataa tactgtaaaa cacaacatat gcagtcacta tgaatcaact acttagatgg   240
tattagtgac ctgtaacaga ctgcagtggt cgaaaaaaaa agcccgcact gtcaggtgcg   300 ggctttttttc tgtgttaagc ttcgacgaat ttctgccatt catccgctta ttatcactta   360

```
ttcaggcgta gcaccaggcg tttaagggca ccaataactg ccttaaaaaa attacgcccc      420
gccctgccac tcatcgcagt actgttgtaa ttcattaagc attctgccga catggaagcc      480
atcacagacg gcatgatgaa cctgaatcgc cagcggcatc agcaccttgt cgccttgcgt      540
ataatatttg cccatggtga aaacgggggc gaagaagttg tccatattgg ccacgtttaa      600
atcaaaactg gtgaaactca cccagggatt ggctgagacg aaaaacatat tctcaataaa      660
ccctttaggg aaataggcca ggttttcacc gtaacacgcc acatcttgcg aatatatgtg      720
tagaaactgc cggaaatcgt cgtggtattc actccagagc gatgaaaacg tttcagtttg      780
ctcatggaaa acggtgtaac aagggtgaac actatcccat atcaccagct caccgtcttt      840
cattgccata cggaattccg gatgagcatt catcaggcgg gcaagaatgt gaataaaggc      900
cggataaaac ttgtgcttat ttttctttac ggtctttaaa aaggccgtaa tatccagctg      960
aacggtctgg ttataggtac attgagcaac tgactgaaat gcctcaaaat gttctttacg     1020
atgccattgg gatatatcaa cggtggtata tccagtgatt tttttctcca ttttagcttc     1080
cttagctcct gaaaatctcg gatccgatat ctagctagcg cgcccggttg acgctgctag     1140
tgttacctag cgatttgtat cttactgcat gttacttcat gttgtcaata cctgtttttc     1200
gtgcgactta tcaggctgtc tacttatccg gagatccaca ggacgggtgt ggtcgccatg     1260
atcgcgtagt cgatagtggc tccaagtagc gaagcgagca ggactgggcg gcggccaaag     1320
cggtcggaca gtgctccgag aacgggtgcg catagaaatt gcatcaacgc atatagcgct     1380
agcagcacgc catagtgact ggcgatgctg tcggaatgga cgatatcccg caagaggccc     1440
ggcagtaccg gcataaccaa gcctatgcct acagcatcca gggtgacggt gccgaggatg     1500
acgatgagcg cattgttaga tttcatacac ggtgcctgac tgcgttagca atttaactgt     1560
gataaactac cgcattaaag cttatcgatg ataagctgtc aaacatgaga attcgaaatc     1620
aaataatgat tttattttga ctgatagtga cctgttcgtt gcaacaaatt gataagcaat     1680
gcttttttat aatgccaact tagtataaaa aagcaggctt caagatcttc acctaccaaa     1740
caatgccccc ctgcaaaaaa taaattcata taaaaaacat acagataacc atctgcggtg     1800
ataaattatc tctggcggtg ttgacataaa taccactggc ggtgatactg agcacatcag     1860
caggacgcac tgaccaccat gaaggtgacg ctcttaaaaa ttaagccctg aagaagggca     1920
gcattcaaag cagaaggctt tggggtgtgt gatacgaaac gaagcattgg ccggaaggag     1980
aactaactat gaatggcgca cagtgggtgg tacatgcgtt gcgggcacag ggtgtgaaca     2040
ccgttttcgg ttatc                                                     2055
```

<210> SEQ ID NO 12
<211> LENGTH: 20
<212> TYPE: DNA
<213> ORGANISM: Artificial Sequence
<220> FEATURE:
<223> OTHER INFORMATION: Primer P5

<400> SEQUENCE: 12

```
gctaagggct aatgagttat                                                   20
```

<210> SEQ ID NO 13
<211> LENGTH: 20
<212> TYPE: DNA
<213> ORGANISM: Artificial Sequence
<220> FEATURE:
<223> OTHER INFORMATION: Primer P6

<400> SEQUENCE: 13
ctcaaaagca gtcaagagtg                                                        20

<210> SEQ ID NO 14
<211> LENGTH: 1850
<212> TYPE: DNA
<213> ORGANISM: Artificial Sequence
<220> FEATURE:
<223> OTHER INFORMATION: PCR product

<400> SEQUENCE: 14
gctaagggct aatgagttat atgcaaatta gtaaaattat gttgctatgt cagatagtta      60
cgatttagtc atctaactat gaagcctgct tttttatact aagttggcat tataaaaaag     120
cattgcttat caatttgttg caacgaacag gtcactatca gtcaaaataa aatcattatt     180
tgatttcgaa ttccccggat ccgtcgacct gcagggggg ggggcgctg aggtctgcct       240 cgtgaagaag gtgttgctga ctcataccag gcctgaatcg ccccatcatc cagccagaaa     300
gtgagggagc cacggttgat gagagctttg ttgtaggtgg accagttggt gattttgaac     360
ttttgctttg ccacggaacg gtctgcgttg tcgggaagat gcgtgatctg atccttcaac     420
tcagcaaaag ttcgatttat tcaacaaagc cgccgtcccg tcaagtcagc gtaatgctct     480
gccagtgtta caaccaatta accaattctg attagaaaaa ctcatcgagc atcaaatgaa     540
actgcaattt attcatatca ggattatcaa taccatattt ttgaaaaagc cgtttctgta     600
atgaaggaga aaactcaccg aggcagttcc ataggatggc aagatcctgg tatcggtctg     660
cgattccgac tcgtccaaca tcaatacaac ctattaattt cccctcgtca aaaataaggt     720
tatcaagtga gaaatcacca tgagtgacga ctgaatccgg tgagaatggc aaaagcttat     780
gcatttcttt ccagacttgt tcaacaggcc agccattacg ctcgtcatca aaatcactcg     840
catcaaccaa accgttattc attcgtgatt gcgcctgagc gagacgaaat acgcgatcgc     900
tgttaaaagg acaattacaa acaggaatcg aatgcaaccg gcgcaggaac actgccagcg     960
catcaacaat attttcacct gaatcaggat attcttctaa tacctggaat gctgttttcc     1020
cggggatcgc agtggtgagt aaccatgcat catcaggagt acggataaaa tgcttgatgg     1080
tcggaagagg cataaattcc gtcagccagt ttagtctgac catctcatct gtaacatcat     1140
tggcaacgct acctttgcca tgtttcagaa acaactctgg cgcatcgggc ttcccataca     1200
atcgatagat tgtcgcacct gattgcccga cattatcgcg agcccattta tacccatata     1260
aatcagcatc catgttggaa tttaatcgcg gcctcgagca agacgtttcc cgttgaatat     1320
ggctcataac accccttgta ttactgttta tgtaagcaga cagttttatt gttcatgatg     1380 atatatttt atcttgtgca atgtaacatc agagattttg agacacaacg tggctttccc      1440 cccccccct gcagtctgtt acaggtcact aataccatct aagtagttga ttcatagtga      1500
ctgcatatgt tgtgttttac agtattatgt agtctgtttt ttatgcaaaa tctaatttaa     1560
tatattgata tttatatcat tttacgtttc tcgttcagct tttttatact aacttgagcg     1620
tctagccctg ttgacaatta atcatcggct cgtataatgt gtggaatcgt gagcggataa     1680
caatttcaca caaataattt tgtttaactt taagaaggag atataatgat cccggacgta     1740
tcacaggcgc tggcctggct ggaaaaacat cctcaggcgt taaaggggat acagcgtggg     1800
ctggagcgcg aaactttgcg tgttaatgct gatggcacac tggcaacaac     1850

<210> SEQ ID NO 15
<211> LENGTH: 64
<212> TYPE: DNA

<213> ORGANISM: Artificial Sequence
<220> FEATURE:
<223> OTHER INFORMATION: Primer P9

<400> SEQUENCE: 15
ctactatctg taggtgttga gagacatcaa gttacacgct caagttagta taaaaaagct        60
gaac                                                                     64

<210> SEQ ID NO 16
<211> LENGTH: 64
<212> TYPE: DNA
<213> ORGANISM: Artificial Sequence
<220> FEATURE:
<223> OTHER INFORMATION: Primer P10

<400> SEQUENCE: 16
cagatcgttg gttaactgct gataaaattc tccacgcata gttagttctc cttccggcca        60
atgc                                                                     64

<210> SEQ ID NO 17
<211> LENGTH: 1969
<212> TYPE: DNA
<213> ORGANISM: Artificial Sequence
<220> FEATURE:
<223> OTHER INFORMATION: PCR product

<400> SEQUENCE: 17
ctactatctg taggtgttga gagacatcaa gttacacgct caagttagta taaaaaagct        60
gaacgagaaa cgtaaaatga tataaatatc aatatattaa attagatttt gcataaaaaa       120
cagactacat aatactgtaa aacacaacat atgcagtcac tatgaatcaa ctacttagat       180
ggtattagtg acctgtaaca gactgcagtg gtcgaaaaaa aaagcccgca ctgtcaggtg       240
cgggcttttt tctgtgttaa gcttcgacga atttctgcca ttcatccgct tattatcact       300
tattcaggcg tagcaccagg cgtttaaggg caccaataac tgccttaaaa aaattacgcc       360
ccgccctgcc actcatcgca gtactgttgt aattcattaa gcattctgcc gacatggaag       420
ccatcacaga cggcatgatg aacctgaatc gccagcggca tcagcacctt gtcgccttgc       480
gtataatatt tgcccatggt gaaaacgggg gcgaagaagt tgtccatatt ggccacgttt       540
aaatcaaaac tggtgaaact cacccaggga ttggctgaga cgaaaaacat attctcaata       600
aaccctttag ggaaataggc caggttttca ccgtaacacg ccacatcttg cgaatatatg       660
tgtagaaact gccggaaatc gtcgtggtat tcactccaga gcgatgaaaa cgtttcagtt       720
tgctcatgga aaacggtgta acaagggtga acactatccc atatcaccag ctcaccgtct       780
ttcattgcca tacggaattc cggatgagca ttcatcaggc gggcaagaat gtgaataaag       840
gccggataaa acttgtgctt atttttcttt acggtcttta aaaaggccgt aatatccagc       900
tgaacggtct ggttataggt acattgagca actgactgaa atgcctcaaa atgttctttta      960 cgatgccatt gggatatatc aacggtggta tatccagtga tttttttctc cattttagct      1020
tccttagctc ctgaaaatct cggatccgat atctagctag agcgcccggt tgacgctgct      1080
agtgttacct agcgatttgt atcttactgc atgttacttc atgttgtcaa tacctgtttt      1140
tcgtgcgact tatcaggctg tctacttatc cggagatcca caggacgggt gtggtcgcca      1200
tgatcgcgta gtcgatagtg gctccaagta gcgaagcgag caggactggg cggcggccaa      1260
agcggtcgga cagtgctccg agaacgggtg cgcatagaaa ttgcatcaac gcatatagcg      1320
ctagcagcac gccatagtga ctggcgatgc tgtcggaatg gacgatatcc cgcaagaggc      1380

```
ccggcagtac cggcataacc aagcctatgc ctacagcatc cagggtgacg gtgccgagga    1440
tgacgatgag cgcattgtta gatttcatac acggtgcctg actgcgttag caatttaact    1500
gtgataaact accgcattaa agcttatcga tgataagctg tcaaacatga gaattcgaaa    1560
tcaaataatg attttatttt gactgatagt gacctgttcg ttgcaacaaa ttgataagca    1620
atgctttttt ataatgccaa cttagtataa aaaagcaggc ttcaagatct tcacctacca    1680
aacaatgccc ccctgcaaaa aataaattca tataaaaaac atacagataa ccatctgcgg    1740
tgataaatta tctctggcgg tgttgacata aataccactg gcggtgatac tgagcacatc    1800
agcaggacgc actgaccacc atgaaggtga cgctcttaaa aattaagccc tgaagaaggg    1860
cagcattcaa agcagaaggc tttggggtgt gtgatacgaa acgaagcatt ggccggaagg    1920
agaactaact atgcgtggag aattttatca gcagttaacc aacgatctg              1969
```

```
<210> SEQ ID NO 18
<211> LENGTH: 20
<212> TYPE: DNA
<213> ORGANISM: Artificial Sequence
<220> FEATURE:
<223> OTHER INFORMATION: Primer P11

<400> SEQUENCE: 18
cctccattag tgggtagcgt                                              20

<210> SEQ ID NO 19
<211> LENGTH: 20
<212> TYPE: DNA
<213> ORGANISM: Artificial Sequence
<220> FEATURE:
<223> OTHER INFORMATION: Primer P12

<400> SEQUENCE: 19
agaatccatt cccgcctttg                                              20

<210> SEQ ID NO 20
<211> LENGTH: 482
<212> TYPE: DNA
<213> ORGANISM: Artificial Sequence
<220> FEATURE:
<223> OTHER INFORMATION: PCR product

<400> SEQUENCE: 20
cctccattag tgggtagcgt tttgatacca actgagatag gaaaaatgat gctttggcat    60
cattttttct ttttatatca atgcagtaaa atcaatcatc attatgccca gccaaaactg   120
tacagttttt ctactatctg taggtgttga gagacatcaa gttacacgtt atttatcctg   180
aattttgcag aagtgttaac gcgttatctc gtcgcgacct ataagtttgg gtaatatgtg   240
ctggaatttg ccctgtctgg agaatcgcaa tgcgtggaga attttatcag cagttaacca   300
acgatctgga aaccgcacgg gcggaagggt gtttaaaga agagcgcatt attacgtctg     360
cgcagcaagc agatatcact gtggctgatg gaagccacgt cattaacttt tgtgccaaca   420
actatctcgg gctggcgaat catcctgatc tgattgcggc ggcaaaggcg ggaatggatt   480
ct                                                                 482

<210> SEQ ID NO 21
<211> LENGTH: 2273
<212> TYPE: DNA
<213> ORGANISM: Artificial Sequence
<220> FEATURE:
```

-continued

<223> OTHER INFORMATION: PCR product

<400> SEQUENCE: 21

```
cctccattag tgggtagcgt tttgatacca actgagatag gaaaaatgat gctttggcat        60
cattttttct ttttatatca atgcagtaaa atcaatcatc attatgccca gccaaaactg       120
tacagttttt ctactatctg taggtgttga gagacatcaa gttacacgct caagttagta       180
taaaaaagct gaacgagaaa cgtaaaatga tataaatatc aatatattaa attagatttt       240
gcataaaaaa cagactacat aatactgtaa aacacaacat atgcagtcac tatgaatcaa       300
ctacttagat ggtattagtg acctgtaaca gactgcagtg gtcgaaaaaa aaagcccgca       360
ctgtcaggtg cgggcttttt tctgtgttaa gcttcgacga atttctgcca ttcatccgct       420
tattatcact tattcaggcg tagcaccagg cgtttaaggg caccaataac tgccttaaaa       480
aaattacgcc ccgccctgcc actcatcgca gtactgttgt aattcattaa gcattctgcc       540
gacatggaag ccatcacaga cggcatgatg aacctgaatc gccagcggca tcagcacctt       600
gtcgccttgc gtataatatt tgcccatggt gaaaacgggg gcgaagaagt tgtccatatt       660
ggccacgttt aaatcaaaac tggtgaaact cacccaggga ttggctgaga cgaaaaacat       720
attctcaata aaccctttag ggaaataggc caggttttca ccgtaacacg ccacatcttg       780
cgaatatatg tgtagaaact gccggaaatc gtcgtggtat tcactccaga gcgatgaaaa       840
cgtttcagtt tgctcatgga aaacggtgta acaaggtgta acactatccc atatcaccag       900
ctcaccgtct ttcattgcca tacggaattc cggatgagca ttcatcaggc gggcaagaat       960
gtgaataaag gccggataaa acttgtgctt atttttcttt acggtcttta aaaaggccgt      1020
aatatccagc tgaacggtct ggttataggt acattgagca actgactgaa atgcctcaaa      1080
atgttcttta cgatgccatt gggatatatc aacggtggta tatccagtga tttttttctc      1140
cattttagct tccttagctc ctgaaaatct cggatccgat atctagctag agcgcccggt      1200
tgacgctgct agtgttacct agcgatttgt atcttactgc atgttacttc atgttgtcaa      1260
tacctgtttt tcgtgcgact tatcaggctg tctacttatc cggagatcca caggacgggt      1320
gtggtcgcca tgatcgcgta gtcgatagtg ctccaagta gcgaagcgag caggactggg      1380
cggcggccaa agcggtcgga cagtgctccg agaacgggtg cgcatagaaa ttgcatcaac      1440
gcatatagcg ctagcagcac gccatagtga ctggcgatgc tgtcggaatg gacgatatcc      1500
cgcaagaggc ccggcagtac cggcataacc aagcctatgc ctacagcatc cagggtgacg      1560
gtgccgagga tgacgatgag cgcattgtta gatttcatac acggtgcctg actgcgttag      1620
caatttaact gtgataaact accgcattaa agcttatcga tgataagctg tcaaacatga      1680
gaattcgaaa tcaaataatg attttatttt gactgatagt gacctgttcg ttgcaacaaa      1740
ttgataagca atgctttttt ataatgccaa cttagtataa aaaagcaggc ttcaagatct      1800
tcacctacca acaatgcccc cctgcaaaa aataaaattca tataaaaaac atacagataa      1860
ccatctgcgg tgataaatta tctctggcgg tgttgacata aataccactg gcggtgatac      1920
tgagcacatc agcaggacgc actgaccacc atgaaggtga cgctcttaaa aattaagccc      1980
tgaagaaggg cagcattcaa agcagaaggc tttggggtgt gtgatacgaa acgaagcatt      2040
ggccggaagg agaactaact atgcgtggag aattttatca gcagttaacc aacgatctgg      2100
aaaccgcacg ggcggaaggg ttgtttaaag aagagcgcat tattacgtct gcgcagcaag      2160
cagatatcac tgtggctgat ggaagccacg tcattaactt ttgtgccaac aactatctcg      2220
ggctggcgaa tcatcctgat ctgattgcgg cggcaaaggc gggaatggat tct           2273
```

-continued

```
<210> SEQ ID NO 22
<211> LENGTH: 65
<212> TYPE: DNA
<213> ORGANISM: Artificial Sequence
<220> FEATURE:
<223> OTHER INFORMATION: Primer P13

<400> SEQUENCE: 22
gttcacaatt cactgcacgt ttcaggaacc atcgctccgc tcaagttagt ataaaaaagc      60
tgaac                                                                  65

<210> SEQ ID NO 23
<211> LENGTH: 64
<212> TYPE: DNA
<213> ORGANISM: Artificial Sequence
<220> FEATURE:
<223> OTHER INFORMATION: Primer P14

<400> SEQUENCE: 23
gccgaagcgc ctttagaaaa tagtcgaatc agtgaatgaa gcctgctttt ttatactaag      60
ttgg                                                                   64

<210> SEQ ID NO 24
<211> LENGTH: 1614
<212> TYPE: DNA
<213> ORGANISM: Artificial Sequence
<220> FEATURE:
<223> OTHER INFORMATION: PCR product

<400> SEQUENCE: 24
gttcacaatt cactgcacgt ttcaggaacc atcgctccgc tcaagttagt ataaaaaagc      60
tgaacgagaa acgtaaaatg atataaatat caatatatta aattagattt tgcataaaaa     120
acagactaca taatactgta aaacacaaca tatgcagtca ctatgaatca actacttaga     180
tggtattagt gacctgtaac agactgcagg gggggggggg aaagccacgt tgtgtctcaa     240
aatctctgat gttacattgc acaagataaa aatatatcat catgaacaat aaaactgtct     300
gcttacataa acagtaatac aaggggtgtt atgagccata ttcaacggga aacgtcttgc     360
tcgaggccgc gattaaattc caacatggat gctgatttat atgggtataa atgggctcgc     420
gataatgtcg ggcaatcagg tgcgacaatc tatcgattgt atgggaagcc cgatgcgcca     480
gagttgtttc tgaaacatgg caaaggtagc gttgccaatg atgttacaga tgagatggtc     540
agactaaact ggctgacgga atttatgcct cttccgacca tcaagcattt tatccgtact     600
cctgatgatg catggttact caccactgcg atccccggga aaacagcatt ccaggtatta     660
gaagaatatc ctgattcagg tgaaaatatt gttgatgcgc tggcagtgtt cctgcgccgg     720
ttgcattcga ttcctgtttg taattgtcct tttaacagcg atcgcgtatt tcgtctcgct     780
caggcgcaat cacgaatgaa taacggtttg gttgatgcga gtgattttga tgacgagcgt     840
aatggctggc ctgttgaaca agtctggaaa gaaatgcata agcttttgcc attctcaccg     900
gattcagtcg tcactcatgg tgatttctca cttgataacc ttatttttga cgaggggaaa     960
ttaataggtt gtattgatgt tggacgagtc ggaatcgcag accgatacca ggatcttgcc    1020
atcctatgga actgcctcgg tgagttttct ccttcattac agaaacggct ttttcaaaaa    1080
tatggtattg ataatcctga tatgaataaa ttgcagtttc atttgatgct cgatgagttt    1140
ttctaatcag aattggttaa ttggttgtaa cactggcaga gcattacgct gacttgacgg    1200
```

-continued

```
gacggcggct ttgttgaata aatcgaactt ttgctgagtt gaaggatcag atcacgcatc      1260
ttcccgacaa cgcagaccgt tccgtggcaa agcaaaagtt caaaatcacc aactggtcca      1320
cctacaacaa agctctcatc aaccgtggct ccctcacttt ctggctggat gatggggcga      1380
ttcaggcctg gtatgagtca gcaacacctt cttcacgagg cagacctcag cgcccccccc      1440
cccctgcagg tcgacggatc cggggaattc gaaatcaaat aatgatttta ttttgactga      1500
tagtgacctg ttcgttgcaa caaattgata agcaatgctt ttttataatg ccaacttagt      1560
ataaaaaagc aggcttcatt cactgattcg actattttct aaaggcgctt cggc           1614

<210> SEQ ID NO 25
<211> LENGTH: 20
<212> TYPE: DNA
<213> ORGANISM: Artificial Sequence
<220> FEATURE:
<223> OTHER INFORMATION: Primer P15

<400> SEQUENCE: 25
cggctttatt cctcttctgc                                                    20

<210> SEQ ID NO 26
<211> LENGTH: 20
<212> TYPE: DNA
<213> ORGANISM: Artificial Sequence
<220> FEATURE:
<223> OTHER INFORMATION: Primer P16

<400> SEQUENCE: 26
taaatattcg cgccagtgcc                                                    20

<210> SEQ ID NO 27
<211> LENGTH: 3136
<212> TYPE: DNA
<213> ORGANISM: Artificial Sequence
<220> FEATURE:
<223> OTHER INFORMATION: PCR product

<400> SEQUENCE: 27
cggctttatt cctcttctgc gggagaggat cagggtgagg aaaatttatg cctcaccctc       60
actctcttcg taaggagaga ggttcacaat tcactgcacg tttcaggaac catcgctcat      120
gacacagacg ttaagccagc ttgaaaacag cggcgctttt attgaacgcc atatcggacc      180
ggacgccgcg caacagcaag aaatgctgaa tgccgttggt gcacaatcgt taaacgcgct      240
gaccggccag attgtgccga aagatattca acttgcgaca ccaccgcagg ttggcgcacc      300
ggcgaccgaa tacgccgcac tggcagaact caaggctatt gccagtcgca ataaacgctt      360
cacgtcttac atcggcatgg gttacaccgc cgtgcagcta ccgccggtta tcctgcgtaa      420
catgctggaa aatccgggct ggtataccgc gtacactccg tatcaacctg aagtctccca      480
gggccgcctt gaagcactgc tcaacttcca gcaggtaacg ctggatttga ctggactgga      540
tatggcctct gcttctcttc tggacgaggc caccgctgcc gccgaagcaa tggcgatggc      600
gaaacgcgtc agcaaactga aaaatgccaa ccgcttcttc gtggcttccg atgtgcatcc      660
gcaaacgctg gatgtggtcc gtactcgtgc cgaaaccttt ggttttgaag tgattgtcga      720
tgacgcgcaa aaagtgctcg accatcagga cgtcttcggc gtgctgttac agcaggtagg      780
cactaccggt gaaattcacg actacactgc gcttattagc gaactgaaat cacgcaaaat      840
tgtggtcagc gttgccgccg atattatggc gctggtgctg ttaactgcgc cgggtaaaca      900
gggcgcggat attgtttttg gttcggcgca acgcttcggc gtgccgatgg gctacggtgg      960
```

-continued

```
cccacacgcg gcattctttg cggcgaaaga tgaatacaaa cgctcaatgc cgggccgtat    1020
tatcggtgta tcgaaagatg cagctggcaa taccgcgctg cgcatggcga tgcagactcg    1080
cgagcaacat atccgccgtg agaaagcgaa ctccaacatt tgtacttccc aggtactgct    1140
ggcaaacatc gccagcctgt atgccgttta tcacggcccg gttggcctga aacgtatcgc    1200
taaccgcatt caccgtctga ccgatatcct ggcggcgggc ctgcaacaaa aaggtctgaa    1260
actgcgccat gcgcactatt tcgacacctt gtgtgtggaa gtggccgaca aagcgggcgt    1320
actgacgcgt gccgaagcgg ctgaaatcaa cctgcgtagc gatattctga acgcggttgg    1380
gatcaccctt gatgaaacaa ccacgcgtga aaacgtaatg cagcttttca acgtgctgct    1440
gggcgataac cacggcctgg acatcgacac gctggacaaa gacgtggctc acgacagccg    1500
ctctatccag cctgcgatgc tgcgcgacga cgaaatcctc acccatccgg tgtttaatcg    1560
ctaccacagc gaaaccgaaa tgatgcgcta tatgcactcg ctggagcgta aagatctggc    1620
gctgaatcag gcgatgatcc cgctgggttc ctgcaccatg aaactgaacg ccgccgccga    1680
gatgatccca atcacctggc cggaatttgc cgaactgcac ccgttctgcc cgccggagca    1740
ggccgaaggt tatcagcaga tgattgcgca gctggctgac tggctggtga aactgaccgg    1800
ttacgacgcc gtttgtatgc agccgaactc tggcgcacag ggcgaatacg cgggcctgct    1860
ggcgattcgt cattatcatg aaagccgcaa cgaagggcat cgcgatatct gcctgatccc    1920
ggcttctgcg cacggaacta accccgcttc tgcacatatg gcaggaatgc aggtggtggt    1980
tgtggcgtgt gataaaaacg gcaacatcga tctgactgat ctgcgcgcga aagcggaaca    2040
ggcgggcgat aacctctcct gtatcatggt gacttatcct tctacccacg gcgtgtatga    2100
agaaacgatc cgtgaagtgt gtgaagtcgt gcatcagttc ggcggtcagg tttaccttga    2160
tggcgcgaac atgaacgccc aggttggcat cacctcgccg ggctttattg gtgcggacgt    2220
ttcacacctt aacctacata aaactttctg cattccgcac ggcggtggtg tccgggtat    2280 gggaccgatc ggcgtgaaag cgcatttggc accgtttgta ccgggtcata gcgtggtgca    2340
aatcgaaggc atgttaaccc gtcagggcgc ggtttctgcg gcaccgttcg gtagcgcctc    2400
tatcctgcca atcagctgga tgtacatccg catgatgggc gcagaagggc tgaaaaaagc    2460
aagccaggtg gcaatcctca cgccaacta tattgccagc cgcctgcagg atgccttccc    2520
ggtgctgtat accggtcgcg acggtcgcgt ggcgcacgaa tgtattctcg atattcgccc    2580
gctgaaagaa gaaaccggca tcagcgagct ggatattgcc aagcgcctga tcgactacgg    2640
tttccacgcg ccgacgatgt cgttcccggt ggcgggtacg ctgatggttg aaccgactga    2700
atctgaaagc aaagtggaac tggatcgctt tatcgacgcg atgctggcta tccgcgcaga    2760
aattgaccag gtgaaagccg gtgtctggcc gctggaagat aacccgctgg tgaacgcgcc    2820
gcacattcag agcgaactgg tcgccgagtg ggcgcatccg tacagccgtg aagttgcggt    2880
attcccggca ggtgtggcag acaaatactg gccgacagtg aaacgtctgg atgatgttta    2940
cggcgaccgt aacctgttct gctcctgcgt accgattagc gaataccagt aattcactga    3000
ttcgactatt ttctaaaggc gcttcggcgc ctttttagtc agatgacaaa gtacaaaagt    3060
gctcagacag tcccctcgcc cctttgggga gagggttagg gtgaggggaa caggccggca    3120
ctggcgcgaa tattta                                                    3136
```

<210> SEQ ID NO 28
<211> LENGTH: 1803
<212> TYPE: DNA

<213> ORGANISM: Artificial Sequence
<220> FEATURE:
<223> OTHER INFORMATION: PCR product

<400> SEQUENCE: 28

```
cggctttatt cctcttctgc gggagaggat cagggtgagg aaaatttatg cctcaccctc      60
actctcttcg taaggagaga ggttcacaat tcactgcacg tttcaggaac catcgctccg     120
ctcaagttag tataaaaaag ctgaacgaga aacgtaaaat gatataaata tcaatatatt     180
aaattagatt ttgcataaaa aacagactac ataatactgt aaaacacaac atatgcagtc     240
actatgaatc aactacttag atggtattag tgacctgtaa cagactgcag ggggggggg     300 gaaagccacg ttgtgtctca aaatctctga tgttacattg cacaagataa aaatatatca     360
tcatgaacaa taaaactgtc tgcttacata aacagtaata caagggggtgt tatgagccat    420 attcaacggg aaacgtcttg ctcgaggccg cgattaaatt ccaacatgga tgctgattta     480
tatgggtata aatgggctcg cgataatgtc gggcaatcag gtgcgacaat ctatcgattg     540
tatgggaagc ccgatgcgcc agagttgttt ctgaaacatg gcaaaggtag cgttgccaat     600
gatgttacag atgagatggt cagactaaac tggctgacgg aatttatgcc tcttccgacc     660
atcaagcatt ttatccgtac tcctgatgat gcatggttac tcaccactgc gatccccggg     720
aaaacagcat tccaggtatt agaagaatat cctgattcag gtgaaaatat tgttgatgcg     780
ctggcagtgt tcctgcgccg gttgcattcg attcctgttt gtaattgtcc ttttaacagc     840
gatcgcgtat ttcgtctcgc tcaggcgcaa tcacgaatga ataacggttt ggttgatgcg     900
agtgattttg atgacgagcg taatggctgg cctgttgaac aagtctggaa agaaatgcat     960
aagcttttgc cattctcacc ggattcagtc gtcactcatg gtgatttctc acttgataac    1020 cttattttttg acgaggggaa attaataggt tgtattgatg ttggacgagt cggaatcgca   1080
gaccgatacc aggatcttgc catcctatgg aactgcctcg gtgagttttc tccttcatta    1140
cagaaacggc tttttcaaaa atatggtatt gataatcctg atatgaataa attgcagttt    1200
catttgatgc tcgatgagtt tttctaatca gaattggtta attggttgta acactggcag    1260
agcattacgc tgacttgacg ggacggcggc tttgttgaat aaatcgaact tttgctgagt    1320
tgaaggatca gatcacgcat cttcccgaca acgcagaccg ttccgtggca aagcaaaagt    1380
tcaaaatcac caactggtcc acctacaaca aagctctcat caaccgtggc tccctcactt    1440
tctggctgga tgatggggcg attcaggcct ggtatgagtc agcaacacct tcttcacgag    1500
gcagacctca gcgccccccc cccctgcag gtcgacggat ccgggaatt cgaaatcaaa      1560 taatgatttt attttgactg atagtgacct gttcgttgca acaaattgat aagcaatgct    1620
tttttataat gccaacttag tataaaaaag caggcttcat tcactgattc gactattttc    1680
taaaggcgct tcggcgcctt tttagtcaga tgacaaagta caaaagtgct cagacagtcc    1740
cctcgcccct ttggggagag ggttagggtg aggggaacag gccggcactg cgcgaatat    1800 tta                                                                 1803
```

<210> SEQ ID NO 29
<211> LENGTH: 458
<212> TYPE: DNA
<213> ORGANISM: Artificial Sequence
<220> FEATURE:
<223> OTHER INFORMATION: PCR product

<400> SEQUENCE: 29

```
tgcaagtgaa gttgagttgt tctggcggtg gaatgatgct cgcaaaaatg cagcggacaa      60
```

-continued

```
aggatgaact acgaggaagg gaacaacatt catacgctca agttagtata aaaaagcagg      120
cttcaagatc ttcacctacc aaacaatgcc cccctgcaaa aaataaattc atataaaaaa      180
catacagata accatctgcg gtgataaatt atctctggcg gtgttgacat aaataccact      240
ggcggtgata ctgagcacat cagcaggacg cactgaccac catgaaggtg acgctcttaa      300
aaattaagcc ctgaagaagg gcagcattca aagcagaagg ctttggggtg tgtgatacga      360
aacgaagcat tggccggaag gagaactaac tatgaatggc gcacagtggg tggtacatgc      420
gttgcgggca cagggtgtga acaccgtttt cggttatc                              458
```

<210> SEQ ID NO 30
<211> LENGTH: 64
<212> TYPE: DNA
<213> ORGANISM: Artificial Sequence
<220> FEATURE:
<223> OTHER INFORMATION: Primer P17

<400> SEQUENCE: 30

```
ggccagtgcc aagcttgcat gcctgcaggt cgactctgaa gcctgctttt ttatactaag       60
ttgg                                                                    64
```

<210> SEQ ID NO 31
<211> LENGTH: 64
<212> TYPE: DNA
<213> ORGANISM: Artificial Sequence
<220> FEATURE:
<223> OTHER INFORMATION: Primer P18

<400> SEQUENCE: 31

```
gtttgcgatg gggtccatca cgatgccgag cttgatcatt atatctcctt cttaaagtta       60
aaca                                                                    64
```

<210> SEQ ID NO 32
<211> LENGTH: 1721
<212> TYPE: DNA
<213> ORGANISM: Artificial Sequence
<220> FEATURE:
<223> OTHER INFORMATION: PCR product

<400> SEQUENCE: 32

```
ggccagtgcc aagcttgcat gcctgcaggt cgactctgaa gcctgctttt ttatactaag       60
ttggcattat aaaaaagcat tgcttatcaa tttgttgcaa cgaacaggtc actatcagtc      120
aaaataaaat cattatttga tttcgaattc cccggatccg tcgacctgca ggggggggggg     180 ggcgctgagg tctgcctcgt gaagaaggtg ttgctgactc ataccaggcc tgaatcgccc      240
catcatccag ccagaaagtg agggagccac ggttgatgag agctttgttg taggtggacc      300
agttggtgat tttgaacttt tgctttgcca cggaacggtc tgcgttgtcg ggaagatgcg      360
tgatctgatc cttcaactca gcaaaagttc gatttattca acaaagccgc cgtcccgtca      420
agtcagcgta atgctctgcc agtgttacaa ccaattaacc aattctgatt agaaaaactc      480
atcgagcatc aaatgaaact gcaatttatt catatcagga ttatcaatac catatttttg      540
aaaaagccgt ttctgtaatg aaggagaaaa ctcaccgagg cagttccata ggatggcaag     600
atcctggtat cggtctgcga ttccgactcg tccaacatca atacaaccta ttaatttccc      660
ctcgtcaaaa ataaggttat caagtgagaa atcaccatga gtgacgactg aatccggtga      720
gaatggcaaa agcttatgca tttctttcca gacttgttca acaggccagc cattacgctc      780
```

-continued

```
gtcatcaaaa tcactcgcat caaccaaacc gttattcatt cgtgattgcg cctgagcgag       840
acgaaatacg cgatcgctgt taaaaggaca attacaaaca ggaatcgaat gcaaccggcg       900
caggaacact gccagcgcat caacaatatt ttcacctgaa tcaggatatt cttctaatac       960
ctggaatgct gttttcccgg ggatcgcagt ggtgagtaac catgcatcat caggagtacg      1020
gataaaatgc ttgatggtcg gaagaggcat aaattccgtc agccagttta gtctgaccat      1080
ctcatctgta acatcattgg caacgctacc tttgccatgt ttcagaaaca actctggcgc      1140
atcgggcttc ccatacaatc gatagattgt cgcacctgat tgcccgacat tatcgcgagc      1200
ccatttatac ccatataaat cagcatccat gttggaattt aatcgcggcc tcgagcaaga      1260
cgtttcccgt tgaatatggc tcataacacc ccttgtatta ctgtttatgt aagcagacag      1320
ttttattgtt catgatgata tattttatc ttgtgcaatg taacatcaga gattttgaga      1380
cacaacgtgg ctttcccccc cccccctgca gtctgttaca ggtcactaat accatctaag      1440
tagttgattc atagtgactg catatgttgt gttttacagt attatgtagt ctgtttttta      1500
tgcaaaatct aatttaatat attgatattt atatcatttt acgtttctcg ttcagctttt      1560
ttatactaac ttgagcgtct agccctgttg acaattaatc atcggctcgt ataatgtgtg      1620
gaatcgtgag cggataacaa tttcacacaa ataattttgt ttaactttaa gaaggagata      1680
taatgatcaa gctcggcatc gtgatggacc ccatcgcaaa c                          1721
```

```
<210> SEQ ID NO 33
<211> LENGTH: 20
<212> TYPE: DNA
<213> ORGANISM: Artificial Sequence
<220> FEATURE:
<223> OTHER INFORMATION: Primer P7

<400> SEQUENCE: 33
ctgagtagga caaatccgcc                                                    20

<210> SEQ ID NO 34
<211> LENGTH: 20
<212> TYPE: DNA
<213> ORGANISM: Artificial Sequence
<220> FEATURE:
<223> OTHER INFORMATION: Primer P8

<400> SEQUENCE: 34
accacgacgc tgtgcttcca                                                    20

<210> SEQ ID NO 35
<211> LENGTH: 274
<212> TYPE: DNA
<213> ORGANISM: Artificial Sequence
<220> FEATURE:
<223> OTHER INFORMATION: PCR product

<400> SEQUENCE: 35
ctgagtagga caaatccgcc gggagcggat ttgaacgttg cgaagcaacg gcccggaggg        60
tggcgggcag gacgcccgcc ataaactgcc aggcatcaaa ttaagcagaa ggccatcctg       120
acggatggcc tttttgcgtg gccagtgcca agcttgcatg cctgcaggtc gactctagat       180
gatcaagctc ggcatcgtga tggaccccat cgcaaacatc aacatcaaga aagattccag       240
ttttgctatg ttgctggaag cacagcgtcg tggt                                   274

<210> SEQ ID NO 36
<211> LENGTH: 1917
```

<212> TYPE: DNA
<213> ORGANISM: Artificial Sequence
<220> FEATURE:
<223> OTHER INFORMATION: PCR product

<400> SEQUENCE: 36

```
ctgagtagga caaatccgcc gggagcggat ttgaacgttg cgaagcaacg gcccggaggg      60
tggcgggcag gacgcccgcc ataaactgcc aggcatcaaa ttaagcagaa ggccatcctg     120
acggatggcc tttttgcgtg gccagtgcca agcttgcatg cctgcaggtc gactctgaag     180
cctgcttttt tatactaagt tggcattata aaaaagcatt gcttatcaat ttgttgcaac     240
gaacaggtca ctatcagtca aaataaaatc attatttgat ttcgaattcc ccggatccgt     300
cgacctgcag ggggggggg gcgctgaggt ctgcctcgtg aagaaggtgt tgctgactca     360
taccaggcct gaatcgcccc atcatccagc cagaaagtga gggagccacg gttgatgaga     420
gctttgttgt aggtggacca gttggtgatt ttgaactttt gctttgccac ggaacggtct     480
gcgttgtcgg gaagatgcgt gatctgatcc ttcaactcag caaaagttcg atttattcaa     540
caaagccgcc gtcccgtcaa gtcagcgtaa tgctctgcca gtgttacaac caattaacca     600
attctgatta gaaaaactca tcgagcatca aatgaaactg caatttattc atatcaggat     660
tatcaatacc atattttga aaaagccgtt tctgtaatga aggagaaaac tcaccgaggc     720
agttccatag gatggcaaga tcctggtatc ggtctgcgat tccgactcgt ccaacatcaa     780
tacaacctat taatttcccc tcgtcaaaaa taaggttatc aagtgagaaa tcaccatgag     840
tgacgactga atccggtgag aatggcaaaa gcttatgcat ttctttccag acttgttcaa     900
caggccagcc attacgctcg tcatcaaaat cactcgcatc aaccaaaccg ttattcattc     960
gtgattgcgc ctgagcgaga cgaaatacgc gatcgctgtt aaaaggacaa ttacaaacag    1020
gaatcgaatg caaccggcgc aggaacactg ccagcgcatc aacaatattt tcacctgaat    1080
caggatattc ttctaatacc tggaatgctg tttttcccggg gatcgcagtg gtgagtaacc    1140
atgcatcatc aggagtacgg ataaaatgct tgatggtcgg aagaggcata aattccgtca    1200
gccagtttag tctgaccatc tcatctgtaa catcattggc aacgctacct ttgccatgtt    1260
tcagaaacaa ctctggcgca tcgggcttcc catacaatcg atagattgtc gcacctgatt    1320
gcccgacatt atcgcgagcc catttatacc catataaatc agcatccatg ttggaattta    1380
atcgcggcct cgagcaagac gtttcccgtt gaatatggct cataacaccc cttgtattac    1440
tgtttatgta agcagacagt tttattgttc atgatgatat attttatct tgtgcaatgt    1500 aacatcagag attttgagac acaacgtggc tttcccccc cccctgcag tctgttacag    1560 gtcactaata ccatctaagt agttgattca tagtgactgc atatgttgtg ttttacagta    1620
ttatgtagtc tgtttttat gcaaaatcta atttaatata ttgatattta tatcatttta    1680
cgtttctcgt tcagcttttt tatactaact tgagcgtcta gccctgttga caattaatca    1740
tcggctcgta taatgtgtgg aatcgtgagc ggataacaat ttcacacaaa taattttgtt    1800
taactttaag aaggagatat aatgatcaag ctcggcatcg tgatggaccc catcgcaaac    1860
atcaacatca agaaagattc cagttttgct atgttgctgg aagcacagcg tcgtggt      1917
```

<210> SEQ ID NO 37
<211> LENGTH: 64
<212> TYPE: DNA
<213> ORGANISM: Artificial Sequence
<220> FEATURE:
<223> OTHER INFORMATION: Primer P19

```
<400> SEQUENCE: 37
cagagcacaa ccacatcaca acaaatccgc gcctgatgaa gcctgctttt ttatactaag        60
ttgg                                                                    64

<210> SEQ ID NO 38
<211> LENGTH: 64
<212> TYPE: DNA
<213> ORGANISM: Artificial Sequence
<220> FEATURE:
<223> OTHER INFORMATION: Primer P20

<400> SEQUENCE: 38
catactttat ttactcccag tgtctgtctc gtaaatcgct caagttagta taaaaaagct        60
gaac                                                                    64

<210> SEQ ID NO 39
<211> LENGTH: 1713
<212> TYPE: DNA
<213> ORGANISM: Artificial Sequence
<220> FEATURE:
<223> OTHER INFORMATION: PCR product

<400> SEQUENCE: 39
cagagcacaa ccacatcaca acaaatccgc gcctgatgaa gcctgctttt ttatactaag        60
ttggcattat aaaaaagcat tgcttatcaa tttgttgcaa cgaacaggtc actatcagtc       120
aaaataaaat cattatttga tttcgaattc tcatgtttga cagcttatca tcgataagct       180
ttaatgcggt agtttatcac agttaaattg ctaacgcagt caggcaccgt gtatgaaatc       240
taacaatgcg ctcatcgtca tcctcggcac cgtcaccctg gatgctgtag gcataggctt       300
ggttatgccg gtactgccgg gcctcttgcg ggatatcgtc cattccgaca gcatcgccag       360
tcactatggc gtgctgctag cgctatatgc gttgatgcaa tttctatgcg cacccgttct       420
cggagcactg tccgaccgct ttggccgccg cccagtcctg ctcgcttcgc tacttggagc       480
cactatcgac tacgcgatca tggcgaccac acccgtcctg tggatctccg ataagtagat       540
cagcctgata agtcgcacga aaaacaggta ttgacaacat gaagtaacat gcagtaagat       600
acaaatcgct aggtaacact agcagcgtca accgggcgct ctagctagag ccaagctagc       660
ttggccggat ccgagatttt caggagctaa ggaagctaaa atggagaaaa aaatcactgg       720
atataccacc gttgatatat cccaatggca tcgtaaagaa cattttgagg catttcagtc       780
agttgctcaa tgtacctata accagaccgt tcagctggat attacggcct ttttaaagac       840
cgtaaagaaa aataagcaca gtttttatcc ggcctttatt cacattcttg cccgcctgat       900
gaatgctcat ccggaattcc gtatggcaat gaaagacggt gagctggtga tatgggatag       960
tgttcaccct tgttacaccg ttttccatga gcaaactgaa acgttttcat cgctctggag      1020
tgaataccac gacgatttcc ggcagtttct acacatatat tcgcaagatg tggcgtgtta      1080
cggtgaaaac ctggcctatt tccctaaagg gtttattgag aatatgtttt tcgtctcagc      1140
caatccctgg gtgagtttca ccagttttga tttaaacgtg gccaatatgg acaacttctt      1200
cgcccccgtt ttcaccatgg gcaaatatta tacgcaaggc gacaaggtgc tgatgccgct      1260
ggcgattcag gttcatcatg ccgtctgtga tggcttccat gtcggcagaa tgcttaatga      1320
attacaacag tactgcgatg agtggcaggg cggggcgtaa ttttttttaag gcagttattg      1380 gtgcccttaa acgcctggtg ctacgcctga ataagtgata ataagcggat gaatggcaga      1440
aattcgtcga agcttaacac agaaaaaagc ccgcacctga cagtgcgggc tttttttttc      1500
```

-continued

```
gaccactgca gtctgttaca ggtcactaat accatctaag tagttgattc atagtgactg    1560
catatgttgt gttttacagt attatgtagt ctgttttta tgcaaaatct aatttaatat    1620
attgatattt atatcatttt acgtttctcg ttcagctttt ttatactaac ttgagcgatt    1680
tacgagacag acactgggag taaataaagt atg                                 1713
```

<210> SEQ ID NO 40
<211> LENGTH: 21
<212> TYPE: DNA
<213> ORGANISM: Artificial Sequence
<220> FEATURE:
<223> OTHER INFORMATION: Primer P21

<400> SEQUENCE: 40

```
ccagtaattc agaaatgttg g                                               21
```

<210> SEQ ID NO 41
<211> LENGTH: 21
<212> TYPE: DNA
<213> ORGANISM: Artificial Sequence
<220> FEATURE:
<223> OTHER INFORMATION: Primer P22

<400> SEQUENCE: 41

```
ccatattacg accatgagtg g                                               21
```

<210> SEQ ID NO 42
<211> LENGTH: 1354
<212> TYPE: DNA
<213> ORGANISM: Artificial Sequence
<220> FEATURE:
<223> OTHER INFORMATION: PCR product

<400> SEQUENCE: 42

```
ccagtaattc agaaatgttg gagaaattat catgatgcaa catcaggtca atgtatcggc     60
tcgcttcaat ccagaaacct tagaacgtgt tttacgcgtg gtgcgtcatc gtggtttcca    120
cgtctgctca atgaatatgg ccgccgccag cgatgcacaa aatataaata tcgaattgac    180
cgttgccagc ccacggtcgg tcgacttact gtttagtcag ttaaataaac tggtggacgt    240
cgcacacgtt gccatctgcc agagcacaac cacatcacaa caaatccgcg cctgagcgca    300
aaaggaatat aaaaatgacc acgaagaaag ctgattacat ttggttcaat ggggagatgg    360
ttcgctggga agacgcgaag gtgcatgtga tgtcgcacgc gctgcactat ggcacttcgg    420
tttttgaagg catccgttgc tacgactcgc acaaaggacc ggttgtattc cgccatcgtg    480
agcatatgca gcgtctgcat gactccgcca aaatctatcg cttcccggtt tcgcagagca    540
ttgatgagct gatggaagct tgtcgtgacg tgatccgcaa aaacaatctc accagcgcct    600
atatccgtcc gctgatcttc gtcggtgatg ttggcatggg agtaaacccg ccagcgggat    660
actcaaccga cgtgattatc gctgctttcc cgtggggagc gtatctgggc gcagaagcgc    720
tggagcaggg gatcgatgcg atggtttcct cctggaaccg cgcacgacca aacaccatcc    780
cgacggcggc aaaagccggt ggtaactacc tctcttccct gctggtgggt agcgaagcgc    840
gccgccacgg ttatcaggaa ggtatcgcgc tggatgtgaa cggttatatc tctgaaggcg    900
caggcgaaaa cctgtttgaa gtgaaagatg gtgtgctgtt caccccaccg ttcacctcct    960
ccgcgctgcc gggtattacc cgtgatgcca tcatcaaact ggcgaaagag ctgggaattg   1020
aagtacgtga gcaggtgctg tcgcgcgaat ccctgtacct ggcggatgaa gtgtttatgt   1080
```

```
ccggtacggc ggcagaaatc acgccagtgc gcagcgtaga cggtattcag gttggcgaag    1140
gccgttgtgg cccggttacc aaacgcattc agcaagcctt cttcggcctc ttcactggcg    1200
aaaccgaaga taaatggggc tggttagatc aagttaatca ataaatacaa aaaatgggac    1260
ggcacgcacc gtcccattta cgagacagac actgggagta aataaagtat gcctaagtac    1320
cgttccgcca ccaccactca tggtcgtaat atgg                                 1354
```

```
<210> SEQ ID NO 43
<211> LENGTH: 2015
<212> TYPE: DNA
<213> ORGANISM: Artificial Sequence
<220> FEATURE:
<223> OTHER INFORMATION: PCR product

<400> SEQUENCE: 43
```

```
ccagtaattc agaaatgttg gagaaattat catgatgcaa catcaggtca atgtatcggc      60
tcgcttcaat ccagaaacct tagaacgtgt tttacgcgtg gtgcgtcatc gtggtttcca     120
cgtctgctca atgaatatgg ccgccgccag cgatgcacaa aatataaata tcgaattgac     180
cgttgccagc ccacggtcgg tcgacttact gtttagtcag ttaaataaac tggtggacgt     240
cgcacacgtt gccatctgcc agagcacaac cacatcacaa caaatccgcg cctgatgaag     300
cctgcttttt tatactaagt tggcattata aaaaagcatt gcttatcaat ttgttgcaac     360
gaacaggtca ctatcagtca aaataaaatc attatttgat ttcgaattct catgtttgac     420
agcttatcat cgataagctt taatgcggta gtttatcaca gttaaattgc taacgcagtc     480
aggcaccgtg tatgaaatct aacaatgcgc tcatcgtcat cctcggcacc gtcaccctgg     540
atgctgtagg cataggcttg gttatgccgg tactgccggg cctcttgcgg gatatcgtcc     600
attccgacag catcgccagt cactatggcg tgctgctagc gctatatgcg ttgatgcaat     660
ttctatgcgc accgttctc ggagcactgt ccgaccgctt tggccgccgc ccagtcctgc      720
tcgcttcgct acttggagcc actatcgact acgcgatcat ggcgaccaca cccgtcctgt     780
ggatctccgg ataagtagac agcctgataa gtcgcacgaa aaacaggtat tgacaacatg     840
aagtaacatg cagtaagata caaatcgcta ggtaacacta gcagcgtcaa ccgggcgctc     900
tagctagagc caagctagct tggccggatc cgagattttc aggagctaag gaagctaaaa     960
tggagaaaaa aatcactgga tataccaccg ttgatatatc ccaatggcat cgtaaagaac    1020
attttgaggc atttcagtca gttgctcaat gtacctataa ccagaccgtt cagctggata    1080
ttacggcctt tttaaagacc gtaaagaaaa ataagcacaa gttttatccg gcctttattc    1140
acattcttgc ccgcctgatg aatgctcatc cggaattccg tatggcaatg aaagacggtg    1200
agctggtgat atgggatagt gttcaccctt gttacaccgt tttccatgag caaactgaaa    1260
cgttttcatc gctctggagt gaataccacg acgatttccg gcagtttcta cacatatatt    1320
cgcaagatgt ggcgtgttac ggtgaaaacc tggcctattt ccctaaaggg tttattgaga    1380
atatgttttt cgtctcagcc aatccctggg tgagtttcac cagttttgat ttaaacgtgg    1440
ccaatatgga caacttcttc gcccccgttt tcaccatggg caaatattat acgcaaggcg    1500
acaaggtgct gatgccgctg gcgattcagg ttcatcatgc cgtctgtgat ggcttccatg    1560
tcggcagaat gcttaatgaa ttacaacagt actgcgatga gtggcagggc ggggcgtaat    1620
ttttttaagg cagttattgg tgcccttaaa cgcctggtgc tacgcctgaa taagtgataa    1680
taagcggatg aatggcagaa attcgtcgaa gcttaacaca gaaaaaagcc cgcacctgac    1740
agtgcgggct tttttttcg accactgcag tctgttacag gtcactaata ccatctaagt    1800
```

-continued

```
agttgattca tagtgactgc atatgttgtg ttttacagta ttatgtagtc tgtttttat      1860 gcaaaatcta atttaatata ttgatattta tatcattta cgtttctcgt tcagctttt       1920 tatactaact tgagcgattt acgagacaga cactgggagt aaataaagta tgcctaagta     1980
ccgttccgcc accaccactc atggtcgtaa tatgg                                2015

<210> SEQ ID NO 44
<211> LENGTH: 60
<212> TYPE: DNA
<213> ORGANISM: Artificial Sequence
<220> FEATURE:
<223> OTHER INFORMATION: Primer P23

<400> SEQUENCE: 44
aattttgttt aactttaaga aggagatata atgatcccgg acgtatcaca ggcgctggcc      60

<210> SEQ ID NO 45
<211> LENGTH: 55
<212> TYPE: DNA
<213> ORGANISM: Artificial Sequence
<220> FEATURE:
<223> OTHER INFORMATION: Primer P24

<400> SEQUENCE: 45
atctaagctt tctagtcagg cgtgttttc cagccacacc gcaaacggtt cggta            55

<210> SEQ ID NO 46
<211> LENGTH: 100
<212> TYPE: DNA
<213> ORGANISM: Artificial Sequence
<220> FEATURE:
<223> OTHER INFORMATION: Ptac4071f10 fragment

<400> SEQUENCE: 46
ccctgttgac aattaatcat cggctcgtat aatgtgtgga atcgtgagcg gataacaatt      60
tcacacaaat aattttgttt aactttaaga aggagatata                            100

<210> SEQ ID NO 47
<211> LENGTH: 45
<212> TYPE: DNA
<213> ORGANISM: Artificial Sequence
<220> FEATURE:
<223> OTHER INFORMATION: Primer P25

<400> SEQUENCE: 47
aacttgagcg tctagccctg ttgacaatta atcatcggct cgtat                      45

<210> SEQ ID NO 48
<211> LENGTH: 100
<212> TYPE: DNA
<213> ORGANISM: Artificial Sequence
<220> FEATURE:
<223> OTHER INFORMATION: Primer P26

<400> SEQUENCE: 48
taatgagtta tatgcaaatt agtaaaatta tgttgctatg tcagatagtt acgatttagt      60
catctaacta tgaagcctgc ttttttatac taagttggca                            100

<210> SEQ ID NO 49
<211> LENGTH: 100
<212> TYPE: DNA
<213> ORGANISM: Artificial Sequence
<220> FEATURE:
```

<223> OTHER INFORMATION: Primer P27

<400> SEQUENCE: 49
taataatatc cacataaata aaacaacggg cgtgttatac gcccgtttca atatttaaca          60
catggagaga tcaggcgtgt ttttccagcc acaccgcaaa                                100

<210> SEQ ID NO 50
<211> LENGTH: 35
<212> TYPE: DNA
<213> ORGANISM: Artificial Sequence
<220> FEATURE:
<223> OTHER INFORMATION: Primer P28

<400> SEQUENCE: 50
gtacccgggg atcctttact gctgctgtaa acgtg                                     35

<210> SEQ ID NO 51
<211> LENGTH: 35
<212> TYPE: DNA
<213> ORGANISM: Artificial Sequence
<220> FEATURE:
<223> OTHER INFORMATION: Primer P29

<400> SEQUENCE: 51
gcctgcaggt cgactatgat caagctcggc atcgt                                     35

<210> SEQ ID NO 52
<211> LENGTH: 27
<212> TYPE: DNA
<213> ORGANISM: Artificial Sequence
<220> FEATURE:
<223> OTHER INFORMATION: Primer P30

<400> SEQUENCE: 52
gacggttttg gcggcgcgtc gattttc                                              27

<210> SEQ ID NO 53
<211> LENGTH: 27
<212> TYPE: DNA
<213> ORGANISM: Artificial Sequence
<220> FEATURE:
<223> OTHER INFORMATION: Primer P31

<400> SEQUENCE: 53
gccgccaaaa ccgtccagcg gcttaag                                              27

<210> SEQ ID NO 54
<211> LENGTH: 55
<212> TYPE: DNA
<213> ORGANISM: Artificial Sequence
<220> FEATURE:
<223> OTHER INFORMATION: Primer P32

<400> SEQUENCE: 54
aattttgttt aactttaaga aggagatata atgatcaagc tcggcatcgt gatgg             55

<210> SEQ ID NO 55
<211> LENGTH: 55
<212> TYPE: DNA
<213> ORGANISM: Artificial Sequence
<220> FEATURE:
<223> OTHER INFORMATION: Primer P33

<400> SEQUENCE: 55
atctaagctt tctagttact gctgctgtaa acgtgcttcg atggcatcca ttaac             55

-continued

```
<210> SEQ ID NO 56
<211> LENGTH: 80
<212> TYPE: DNA
<213> ORGANISM: Artificial Sequence
<220> FEATURE:
<223> OTHER INFORMATION: Primer P34

<400> SEQUENCE: 56
ttaccgcgct acaagtacga tttggcgatt tgggctaacg gagaagaata tgaagcctgc      60
ttttttatac taagttggca                                                  80

<210> SEQ ID NO 57
<211> LENGTH: 90
<212> TYPE: DNA
<213> ORGANISM: Artificial Sequence
<220> FEATURE:
<223> OTHER INFORMATION: Primer P35

<400> SEQUENCE: 57
aagggcgctg tcactcagag tctcaacgag atccttctcg ctaaggtggg ttactgctgc      60
tgtaaacgtg cttcgatggc atccattaac                                       90

<210> SEQ ID NO 58
<211> LENGTH: 1791
<212> TYPE: DNA
<213> ORGANISM: Artificial Sequence
<220> FEATURE:
<223> OTHER INFORMATION: PCR product

<400> SEQUENCE: 58
agtttgatcg cgctaaatac tgcttcacca caaggacgct caagttagta taaaaaagct      60
gaacgagaaa cgtaaaatga tataaatatc aatatattaa attagatttt gcataaaaaa     120
cagactacat aatactgtaa aacacaacat atgcagtcac tatgaatcaa ctacttagat     180
ggtattagtg acctgtaaca gactgcagtg gtcgaaaaaa aaagcccgca ctgtcaggtg     240
cgggcttttt tctgtgttaa gcttcgacga atttctgcca ttcatccgct tattatcact     300
tattcaggcg tagcaccagg cgtttaaggg caccaataac tgccttaaaa aaattacgcc     360
ccgccctgcc actcatcgca gtactgttgt aattcattaa gcattctgcc gacatggaag     420
ccatcacaga cggcatgatg aacctgaatc gccagcggca tcagcacctt gtcgccttgc     480
gtataatatt tgcccatggt gaaaacgggg gcgaagaagt tgtccatatt ggccacgttt     540
aaatcaaaac tggtgaaact cacccaggga ttggctgaga cgaaaaacat attctcaata     600
aaccctttag ggaaataggc caggttttca ccgtaacacg ccacatcttg cgaatatatg     660
tgtagaaact gccggaaatc gtcgtggtat tcactccaga gcgatgaaaa cgtttcagtt     720
tgctcatgga aaacggtgta acaagggtga acactatccc atatcaccag ctcaccgtct     780
ttcattgcca tacggaattc cggatgagca ttcatcaggc gggcaagaat gtgaataaag     840
gccggataaa acttgtgctt attttttcttt acggtcttta aaaaggccgt aatatccagc     900
tgaacggtct ggttataggt acattgagca actgactgaa atgcctcaaa atgttcttta     960
cgatgccatt gggatatatc aacggtggta tatccagtga tttttttctc cattttagct    1020
tccttagctc ctgaaaatct cggatccgat atctagctag agcgcccggt tgacgctgct    1080
agtgttacct agcgatttgt atcttactgc atgttacttc atgttgtcaa tacctgtttt    1140
tcgtgcgact tatcaggctg tctacttatc cggagatcca caggacgggt gtggtcgcca    1200
```

-continued

```
tgatcgcgta gtcgatagtg gctccaagta gcgaagcgag caggactggg cggcggccaa      1260
agcggtcgga cagtgctccg agaacgggtg cgcatagaaa ttgcatcaac gcatatagcg      1320
ctagcagcac gccatagtga ctggcgatgc tgtcggaatg gacgatatcc cgcaagaggc      1380
ccggcagtac cggcataacc aagcctatgc ctacagcatc cagggtgacg gtgccgagga      1440
tgacgatgag cgcattgtta gatttcatac acggtgcctg actgcgttag caatttaact      1500
gtgataaact accgcattaa agcttatcga tgataagctg tcaaacatga gaattcgaaa      1560
tcaaataatg attttatttt gactgatagt gacctgttcg ttgcaacaaa ttgataagca      1620 atgcttttttt ataatgccaa cttagtataa aaaagcaggc ttcaagatct ctcacctacc      1680
aaacaatgcc cccctgcaaa aaataaaattc ataaaaaaca tacagataac catctgcggt      1740
gataaattat ctctggcggt gttgacaatt aatcatcggc tcgtataatg t              1791
```

```
<210> SEQ ID NO 59
<211> LENGTH: 500
<212> TYPE: DNA
<213> ORGANISM: Artificial Sequence
<220> FEATURE:
<223> OTHER INFORMATION: PCR product

<400> SEQUENCE: 59
tctgctcaat cagcacaact tcatcacgca ctgggtcaaa gggtagcaag actgcggcgt        60
gaccgcgctc aaaaatttcc cgccgcacct catgactcat ttgcccgttg aatagacgat       120
gacgaaatct ataaagatct aatgaaaaaa agccgcgata aagtgtttct cgtgcaataa       180
tttctacatc gttttttgcca aatgtaacgg gcaggttgtc tggcttaagc attgttaatg      240
tcctggcact aatagtgaat taaatgtgaa tttcagcgac gtttgactgc cgtttgagca       300
gtcatgtgtt aaattgaggc acattaacgc cctatggcac gtaacgccaa ccttttgcgg       360
tagcggcttc tgctagaatc cgcaataatt ttacagtttg atcgcgctaa atactgcttc       420
accacaagga atgcaaatga agaaattgct ccccattctt atcggcctga gcctttctgg       480
gttcagttcg ttgagccagg                                                    500
```

```
<210> SEQ ID NO 60
<211> LENGTH: 2279
<212> TYPE: DNA
<213> ORGANISM: Artificial Sequence
<220> FEATURE:
<223> OTHER INFORMATION: PCR product

<400> SEQUENCE: 60
tctgctcaat cagcacaact tcatcacgca ctgggtcaaa gggtagcaag actgcggcgt        60
gaccgcgctc aaaaatttcc cgccgcacct catgactcat ttgcccgttg aatagacgat       120
gacgaaatct ataaagatct aatgaaaaaa agccgcgata aagtgtttct cgtgcaataa       180
tttctacatc gttttttgcca aatgtaacgg gcaggttgtc tggcttaagc attgttaatg      240
tcctggcact aatagtgaat taaatgtgaa tttcagcgac gtttgactgc cgtttgagca       300
gtcatgtgtt aaattgaggc acattaacgc cctatggcac gtaacgccaa ccttttgcgg       360
tagcggcttc tgctagaatc cgcaataatt ttacagtttg atcgcgctaa atactgcttc       420
accacaagga cgctcaagtt agtataaaaa agctgaacga gaaacgtaaa atgatataaa       480
tatcaatata ttaaattaga ttttgcataa aaaacagact acataatact gtaaaacaca       540
acatatgcag tcactatgaa tcaactactt agatggtatt agtgacctgt aacagactgc       600
agtggtcgaa aaaaaaagcc cgcactgtca ggtgcgggct tttttctgtg ttaagcttcg       660
```

-continued

```
acgaatttct gccattcatc cgcttattat cacttattca ggcgtagcac caggcgttta      720
agggcaccaa taactgcctt aaaaaaatta cgccccgccc tgccactcat cgcagtactg      780
ttgtaattca ttaagcattc tgccgacatg gaagccatca cagacggcat gatgaacctg      840
aatcgccagc ggcatcagca ccttgtcgcc ttgcgtataa tatttgccca tggtgaaaac      900
gggggcgaag aagttgtcca tattggccac gtttaaatca aaactggtga aactcaccca      960
gggattggct gagacgaaaa acatattctc aataaaccct ttagggaaat aggccaggtt     1020
ttcaccgtaa cacgccacat cttgcgaata tatgtgtaga aactgccgga aatcgtcgtg     1080
gtattcactc cagagcgatg aaaacgtttc agtttgctca tggaaaacgg tgtaacaagg     1140
gtgaacacta tcccatatca ccagctcacc gtctttcatt gccatacgga attccggatg     1200
agcattcatc aggcgggcaa gaatgtgaat aaaggccgga taaaacttgt gcttattttt     1260
ctttacggtc tttaaaaagg ccgtaatatc cagctgaacg gtctggttat aggtacattg     1320
agcaactgac tgaaatgcct caaaatgttc tttacgatgc cattgggata tatcaacggt     1380
ggtatatcca gtgatttttt tctccatttt agcttcctta gctcctgaaa atctcggatc     1440
cgatatctag ctagagcgcc cggttgacgc tgctagtgtt acctagcgat ttgtatctta     1500
ctgcatgtta cttcatgttg tcaatacctg tttttcgtgc gacttatcag gctgtctact     1560
tatccggaga tccacaggac gggtgtggtc gccatgatcg cgtagtcgat agtggctcca     1620
agtagcgaag cgagcaggac tgggcggcgg ccaaagcggt cggacagtgc tccgagaacg     1680
ggtgcgcata gaaattgcat caacgcatat agcgctagca gcacgccata gtgactggcg     1740
atgctgtcgg aatggacgat atcccgcaag aggcccggca gtaccggcat aaccaagcct     1800
atgcctacag catccagggt gacggtgccg aggatgacga tgagcgcatt gttagatttc     1860
atacacggtg cctgactgcg ttagcaattt aactgtgata aactaccgca ttaaagctta     1920
tcgatgataa gctgtcaaac atgagaattc gaaatcaaat aatgatttta ttttgactga     1980
tagtgacctg ttcgttgcaa caaattgata agcaatgctt ttttataatg ccaacttagt     2040
ataaaaaagc aggcttcaag atctctcacc taccaaacaa tgcccccctg caaaaaataa     2100
attcataaaa aacatacaga taaccatctg cggtgataaa ttatctctgg cggtgttgac     2160
aattaatcat cggctcgtat aatgtgtgga attgtgataa ggaggtgata tgcaaatgaa     2220
gaaattgctc cccattctta tcggcctgag cctttctggg ttcagttcgt tgagccagg      2279
```

```
<210> SEQ ID NO 61
<211> LENGTH: 60
<212> TYPE: DNA
<213> ORGANISM: Artificial Sequence
<220> FEATURE:
<223> OTHER INFORMATION: Primer P36

<400> SEQUENCE: 61
agtttgatcg cgctaaatac tgcttcacca caaggacgct caagttagta taaaaaagct       60

<210> SEQ ID NO 62
<211> LENGTH: 70
<212> TYPE: DNA
<213> ORGANISM: Artificial Sequence
<220> FEATURE:
<223> OTHER INFORMATION: Primer P37

<400> SEQUENCE: 62
gccgataaga atggggagca atttcttcat ttgcatatca cctccttatc acaattccac       60
```

-continued

```
acattatacg                                                              70

<210> SEQ ID NO 63
<211> LENGTH: 20
<212> TYPE: DNA
<213> ORGANISM: Artificial Sequence
<220> FEATURE:
<223> OTHER INFORMATION: Primer P38

<400> SEQUENCE: 63
tctgctcaat cagcacaact                                                   20

<210> SEQ ID NO 64
<211> LENGTH: 19
<212> TYPE: DNA
<213> ORGANISM: Artificial Sequence
<220> FEATURE:
<223> OTHER INFORMATION: Primer P39

<400> SEQUENCE: 64
cctggctcaa cgaactgaa                                                    19
```